United States Patent
Walzl et al.

(10) Patent No.: US 10,001,481 B2
(45) Date of Patent: Jun. 19, 2018

(54) METHOD FOR DIAGNOSING TUBERCULOSIS DISEASE BY DETECTING INDUCED MARKERS AFTER STIMULATION OF T-CELLS WITH ANTIGENS

(71) Applicant: STELLENBOSCH UNIVERSITY, Western Cape Province (ZA)

(72) Inventors: Gerhard Walzl, Cape Town (ZA); Novel Njweipi Chegou, Cape Town (ZA); Paulin Essone Ndong, Parow (ZA)

(73) Assignee: Stellenbosch University, Stellenbosch Western Cape Province (ZA)

( * ) Notice: Subject to any disclaimer, the term of this patent is extended or adjusted under 35 U.S.C. 154(b) by 139 days.

(21) Appl. No.: 14/403,659

(22) PCT Filed: May 27, 2013

(86) PCT No.: PCT/IB2013/054377
§ 371 (c)(1),
(2) Date: Nov. 25, 2014

(87) PCT Pub. No.: WO2013/175459
PCT Pub. Date: Nov. 28, 2013

(65) Prior Publication Data
US 2015/0141279 A1    May 21, 2015

(30) Foreign Application Priority Data
May 25, 2012 (ZA) .................................. 2012/03837

(51) Int. Cl.
| | | |
|---|---|---|
| A61K 39/04 | (2006.01) | |
| A61K 39/02 | (2006.01) | |
| A61K 39/00 | (2006.01) | |
| G01N 33/569 | (2006.01) | |
| G01N 33/543 | (2006.01) | |

(52) U.S. Cl.
CPC ......... *G01N 33/5695* (2013.01); *A61K 39/04* (2013.01); *G01N 33/543* (2013.01); *G01N 2469/00* (2013.01)

(58) Field of Classification Search
CPC ............................... A61K 39/00; A61K 39/04
USPC ..................... 424/184.1, 234.1, 248.1; 435/4
See application file for complete search history.

(56) References Cited

PUBLICATIONS

Mueller, H., et al. Cytokine, vol. 43, No. 2, pp. 143-148, Aug. 2008.*

Sebastian D. Schuck et al: "Identification of T-Cell Antigens Specific for Latent *Mycobracterium tuberculosis* Infection", PLOS ONE, vol. 4, No. 5, May 18, 2009 (May 18, 2009), p. e5590, XP055073272, D01: 10.1371/journal.pone.0005590, table 1, fig. 1-2.
"Abstracts of the 22nd European Congress of Clinical Microbiology and Infectious Diseases", Clinical Microbiology and Infection, vol. 18, Apr. 1, 2012 (Apr. 1, 2012), pp. 1-113, XP055073315, ISSN: 1198-743X, D01: 10.1111/j.1469-0691.2012.03801.x 0229.
Novel N Chegou et al: "Potential of novel *Mycobacterium tuberculosis* infection phase-dependent antigens in the diagnosis of TB disease in a high burden setting", BMC Infectious Diseases, Biomed Central, London, GB, vol. 12, No. 1, Jan. 20, 2012 (Jan. 20, 2012), p. 10, XP021130535, ISSN: 1471-2334, DOI: 10.1186/1471-2334-12-10 p. 2-p. 5.
J. Lighter et al: "Chemokine IP-10: an adjunct marker for latent tuberculosis infection in children", Int J Tuberc Lung Dis, vol. 13, No. 6, Jun. 1, 2009 (Jun. 1, 2009), pp. 731-736, XP055073278, p. 734.
Morten Ruhwald et al: "IP-10 release assays in the diagnosis of tuberculosis infection: current status and future directions", Expert Review of Molecular Diagnostics, vol. 12, No. 2, Mar. 1, 2012 (Mar. 1, 2012), pp. 175-187, XP055073280, ISSN: 1473-7159, D01: 10.1586/erm.11.97 p. 181.
Novel N. Chegou et al: "Potential of Host Markers Produced by Infection Phase-Dependent Antigen-Stimulated Cells for the Diagnosis of Tuberculosis in a Highly Endemic Area", PLOS ONE, vol. 7, No. 6, Jun. 5, 2012 (Jun. 5, 2012), p. e38501, XP055073499, D01: 10.1371/journal.pone.0038501—the whole document.
Chegou, N. N., Black, G. F., Kidd, M., van Heiden, P. D. & Walzl, G. Host markers in QuantiFERON supernatants differentiate active TB from latent TB infection: preliminary report. BMC Pulm Med 9, 21 (2009).
International Search Report for PCT/IB2013/054377 dated Jan. 9, 2014.
Written Opinion for PCT/IB2013/054377 dated Jan. 9, 2014.

* cited by examiner

*Primary Examiner* — Rodney P Swartz
(74) *Attorney, Agent, or Firm* — Andrus Intellectual Property Law, LLP

(57) ABSTRACT

A method of diagnosing tuberculosis (TB) disease and distinguishing between active TB and latent TB infection in a subject is described herein. A sample from the subject is stimulated with at least one *Mycobacterium tuberculosis* (*M.tb*) infection phase-dependent antigen selected from Rv0081, Rv2032, Rv1737c, Rv2389c, Rv0867c, TB18.2, Rv2099c, Rv1733c, *M.tb* PPD, PHA and ESAT-6/CFP-10 and the presence of at least one host marker in the sample is detected, the host marker being selected from EGF, TGF-α, TNF-α, VEGF, RANTES, IL-12(p40), IL-12(p70), IL-10, IP-10, IFN-α2, fractalkine, IFN-γ, IL-13, IL-1Ra, IL-3, IL-4, IL-5, MIP-1α, ENA-78, BCA-1, TARC, X6-Ckine, eotaxin, eotaxin-2, SCF, APOA-1, APOE, HPALBN, HCF, Serum amyloid protein A (SAA), C-reactive protein (CRP), serum amyloid protein P (SAP), TIMP-1, MIP-1β, IL-6, GM-CSF, IL-1α, MMP-9, MMP-2, MCP-1, TRAIL, IL-15, IL-17F, IL-22, TNF-β, MCP-2 and MCP-4. Additional host markers may also be detected in an unstimulated sample from the subject.

19 Claims, 4 Drawing Sheets

METHOD FOR DIAGNOSING TUBERCULOSIS DISEASE BY DETECTING INDUCED MARKERS AFTER STIMULATION OF T-CELLS WITH ANTIGENS

CROSS REFERENCE TO RELATED APPLICATION

The present application is the U.S. national stage application of International Application PCT/IB2013/054377, filed May 27, 2013, which international application was published on Nov. 28, 2013, as International Publication WO2013/175459. The International Application claims priority of South African Patent Application No. 2012/03837, filed May 25, 2012, the contents of which are incorporated herein by reference in their entireties.

FIELD OF THE INVENTION

This invention relates to a method for diagnosing tuberculosis disease and not merely identifying *Mycobacterium tuberculosis* infection in a subject, by identifying host markers produced by infection phase-dependent antigen-stimulated cells, and to a device and kit for use in the method.

BACKGROUND TO THE INVENTION

The diagnosis of tuberculosis (TB) is still a major challenge, especially in resource-constrained settings[1]. Sputum based tests are widely used to diagnose active TB, but most of these tests have serious limitations: staining for acid fast bacilli (AFB), the most widely used test, has poor sensitivity[2]. Bacterial culture from sputum remains the gold standard method for TB diagnosis, but might fail to deliver results in a time effective manner. The automated real-time sputum processing molecular beacon assay, XpertMTB/RIF assay (Cepheid Inc., CA, USA) yields results within 2 hours with high sensitivity and specificity (98-100%) in smear positive cases, but only moderate sensitivity (68-72%) in smear negative TB cases[2]. Cost effectiveness of the GeneXpert test remains one of the major impediments to the large-scale roll-out of the test in high burden but resource-constrained settings. Furthermore, sputum based tests (including the GeneXpert) have limited clinical utility in individuals with difficulty in providing good quality sputum samples, such as children and those with extra pulmonary TB disease. Immunological tests may be beneficial in such cases (especially if they are developed into rapid, point-of-care tests). However, serological tests have shown high variability—sensitivity between 10% and 90% and specificity between 47% and 100%[5]—and therefore have limited utility clinically and have been prohibited by the WHO[11].

T-cell based immunological assays such as the interferon gamma (IFN-γ) release assays (IGRAs) added a new value to immunological diagnosis of TB, especially when compared to the traditional skin test (TST)[12]. This is due to the use of highly immunogenic *Mycobacterium tuberculosis* (*M.tb*) specific antigens: the 6-kDa early secretory antigenic target (ESAT-6), 10-kDa culture filtrate protein (CFP-10) and TB7.7 (Rv2654), the latter only being used in the Quantiferon TB Gold In Tube (QFT-IT) test. However, IGRAs do not differentiate between active TB disease and latent *M.tb* infection and although useful in low incidence settings, they are not recommended for high burden settings and therefore only used for research purposes in high burden areas[26].

There is therefore a need for a method for diagnosing TB disease, which will be suitable for use in resource limited settings and which can distinguish between latent infection and active disease.

SUMMARY OF THE INVENTION

According to a first embodiment of the invention, there is provided a method of diagnosing tuberculosis (TB) disease in a subject, the method comprising the steps of:
contacting a sample from the subject with at least one *Mycobacterium tuberculosis* (*M.tb*) infection phase-dependent antigen selected from Rv0081, Rv2032, Rv1737c, Rv2389c, Rv0867c, ESAT-6/CFP-10, Rv2029c, Rv1733c, TB18.2, *M.tb* PPD and phytohaemagglutinin (PHA); and
detecting, measuring or analyzing the absence, presence or level of one or more antigen-specific host markers in the sample, the one or more host markers being selected from EGF, TGF-α, TNF-α, VEGF, RANTES, IL-12 (p40), IL-12(p70), IL-10, IP-10, IFN-α2, fractalkine, IFN-γ, IL-13, IL-1Ra, IL-3, IL-4, IL-5, MIP-1α, ENA-78, BCA-1, TARC, X6-Ckine, eotaxin, eotaxin-2, SCF, APOA-1, APOE, HPALBN, HCF, Serum amyloid protein A (SAA), C-reactive protein (CRP), serum amyloid protein P (SAP), TIMP-1, MIP-1β, IL-6, GM-CSF, IL-1α, MMP-9, MMP-2, MCP-1, TRAIL, IL-15, IL-17F, IL-22, TNF-β, MCP-2 and MCP-4;
wherein the absence, presence or level of the host marker(s) indicates that the subject has TB disease, and wherein TB disease is distinguished from latent *Mycobacterium tuberculosis* infection.

More particularly, the host markers may be selected from one or more of IFN-γ, IL-13, IL-1Ra, IL-5, MIP-1α, MIP-1β, VEGF, ENA-78, BCA-1, X6-Ckine, eotaxin-2, SCF, APOE, HPALBN, SAA, CRP, SAP, TIMP-1, IP-10, IL-1α, TNF-α, EGF, TNF-α, TGF-α, IL-10 and IL-12(p40/p70).

The method may also comprise a step of detecting one or more host markers in an unstimulated sample.

The absence, presence or level of the host marker(s) in the sample may be compared to the level of the same host marker(s) in a subject without TB disease. This subject may nevertheless have latent *Mycobacterium tuberculosis* infection (LTBI).

The method may include the step of indicating to a user whether the subject has TB disease or not. An indicator may be used to indicate whether the level of the host marker is above or below a cut-off level which differentiates between TB disease and no TB disease. The indicator may be a chromatographic indicator.

The method may be for use in diagnosing TB disease in populations or areas where there is a high prevalence of LTBI.

The sample and antigen may be incubated together at about 37° C. overnight or for a period of from about 6 to about 24 hours.

The method may be used for diagnosing both pulmonary and extrapulmonary TB disease, and may also be suitable for use in children.

The sample may be whole blood or blood cells, or fluid from the pleural space, the pericardial space, abdominal cavity or sub-arachnoid space. More preferably, the sample is blood. The sample may be diluted or undiluted.

When the antigen is Rv0081, the host marker is preferably selected from one or more of IP-10, IL-10, IL-12(p40), TNF-α, IFN-α2, VEGF, RANTES, IL-6, MCP-1, MIP-1α, MIP-1β, ENA-78, X6-Ckine.

When the antigen is Rv2032, the host marker is preferably selected from one or more of TNF-α, TGF-α, IL-10, IL-12 (p40), fractalkine, VEGF, RANTES, MMP-2, SAP and EGF.

When the antigen is Rv1737c, the host marker is preferably selected from one or more of IL-10, TGF-α, TNF-α, IL-12(p40) and EGF.

When the antigen is Rv2389c, the host marker is preferably selected from one or more of IFN-γ TGF-α, TNF-α, VEGF, IL-10, RANTES, CRP, SAP, EGF and MMP-9.

When the antigen is Rv0867c, the host marker is preferably selected from one or more of TGF-α, IFN-γ and fractalkine.

When the antigen is Rv1733c, the host marker is preferably selected from one or more of IL-6, TNF-α, X6-Ckine, SCF and IL-22.

When the antigen is Rv2029c, the host marker is preferably selected from one or more of ENA-78, X6-Ckine, MCP-4 and SCF.

When the antigen is TB18.2, the host marker is preferably selected from one or more of GM-CSF, IL-15, IFN-γ, IL-12(p70), IL-5, IL-13 and eotaxin-3.

When the antigen is ESAT-6/CFP-10, the host marker is preferably selected from one or more of X6-Ckine, HCFH and HCC3.

When the antigen is *M.tb* PPD, the host marker is preferably selected from one or more of VEGF, IL-13, TARC and SCF.

When the antigen is PHA, the host marker is preferably selected from one or more of BCA-1, TRAIL, APOE, HPALBN and IL-4.

The one or more host markers detected in the unstimulated sample are preferably selected from one or more of CRP, SAA, SAA, TIMP-1, BCA-1, ENA-78, IL-1α, MMP-2, IFN-α2 and fractalkine.

The sample may be contacted with any one of the antigens or with a combination of any two, three, four or five of the antigens.

According to a second embodiment of the invention, there is provided a *Mycobacterium tuberculosis* (*M.tb*) infection phase-dependent antigen or combinations of antigens selected from the group consisting of Rv0081, Rv2032, Rv1737c, Rv2389c, Rv0867c TB18.2, Rv2099c, Rv1733c, *M.tb* PPD, PHA and ESAT-6/CFP-10 for use in a method of diagnosing TB disease.

According to a third embodiment of the invention, there is provided a kit for diagnosing TB disease in a subject, the kit comprising:
  one or more *Mycobacterium tuberculosis* (*M.tb*) infection phase-dependent antigens selected from Rv0081, Rv2032, Rv1737c, Rv2389c, Rv0867c, TB18.2, Rv2099c, Rv1733c, *M.tb* PPD, PHA and ESAT-6/CFP-10; and
  means for detecting the absence or presence of at least one host marker in a sample from the subject which has been stimulated with the one or more antigens, the host marker being selected from the group consisting of EGF, TGF-α, TNF-α, VEGF, RANTES, IL-12(p40), IL-12(p70), IL-10, IP-10, IFN-α2, fractalkine, IFN-γ, IL-13, IL-1Ra, IL-3, IL-4, IL-5, MIP-1α, ENA-78, BCA-1, TARC, X6-Ckine, eotaxin, eotaxin-2, SCF, APOA-1, APOE, HPALBN, HCF, Serum amyloid protein A (SAA), C-reactive protein (CRP), serum amyloid protein P (SAP), TIMP-1, MIP-1β, IL-6, GM-CSF, IL-1α, MMP-9, MMP-2, MCP-1, TRAIL, IL-15, IL-17F, IL-22, TNF-β, MCP-2 and MCP-4.

The kit may further comprise a receptacle into which the sample from the subject can be placed, wherein the one or more antigens are located in the receptacle.

According to a fourth embodiment of the invention, there is provided a device for diagnosing TB disease according to the method described above, the device comprising:
  a loading zone which can be brought into contact with a sample which has been stimulated with one or more antigens selected from the group consisting of Rv0081, Rv2032, Rv1737c, Rv2389c, Rv0867c, TB18.2, Rv2099c, Rv1733c, *M.tb* PPD, PHA and ESAT-6/CFP-10,
  a detecting zone which detects whether one or more host markers selected from the group consisting of EGF, TGF-α, TNF-α, VEGF, RANTES, IL-12(p40), IL-12 (p70), IL-10, IP-10, IFN-α2, fractalkine, IFN-γ, IL-13, IL-1Ra, IL-3, IL-4, IL-5, MIP-1α, ENA-78, BCA-1, TARC, X6-Ckine, eotaxin, eotaxin-2, SCF, APOA-1, APOE, HPALBN, HCF, Serum amyloid protein A (SAA), C-reactive protein (CRP), serum amyloid protein P (SAP), TIMP-1, MIP-1β, IL-6, GM-CSF, IL-1α, MMP-9, MMP-2, MCP-1, TRAIL, IL-15, IL-17F, IL-22, TNF-β, MCP-2 and MCP-4 are present in the sample, and
  an indicating zone which indicates if one or more of the host markers has been detected.

The detecting zone and indicating zone may be the same or different zones.

A visual change in the indicating zone may indicate to a user that a subject from which the sample was taken has TB disease.

The device may be a dip stick, test strip or any other suitable device.

DETAILED DESCRIPTION OF THE INVENTION

Figure 1:
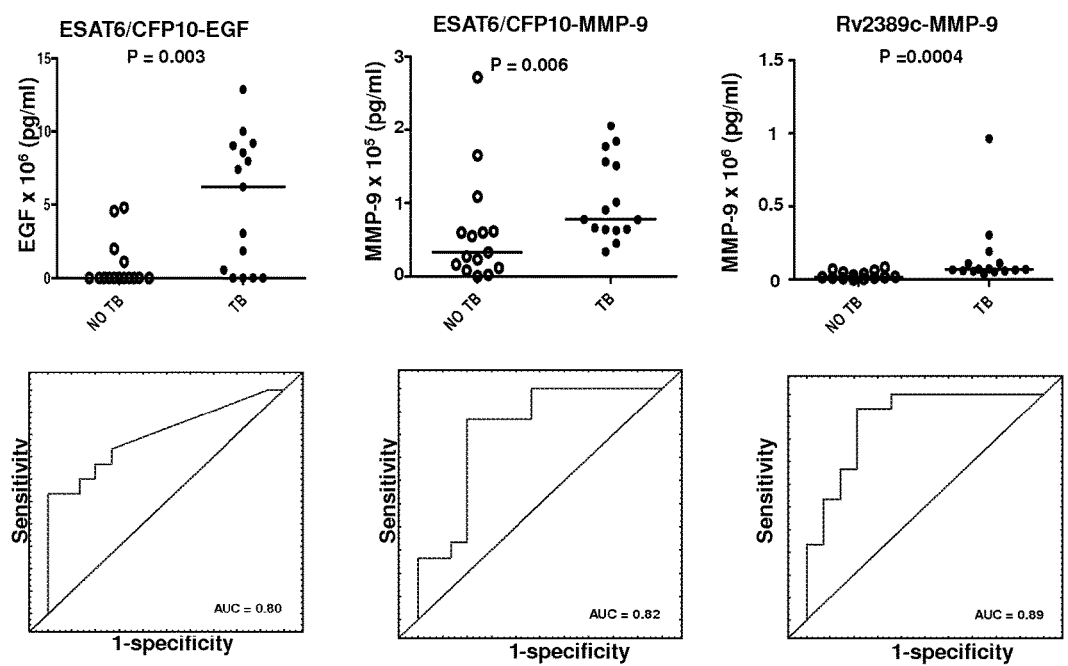
FIG. 1: Representative scatter-dot plots showing levels of analytes in 7-day culture supernatants and ROC curves for accuracy in the diagnosis of TB disease. Error bars in the scatter dot plots represent the median analyte levels. Some analytes with AUC≥0.80 are shown.

A method of diagnosing tuberculosis (TB) disease in a subject is described herein. According to the method, a sample from the subject is stimulated with at least one *Mycobacterium tuberculosis* (*M.tb*) infection phase-dependent antigen selected from Rv0081, Rv2032, Rv1737c, Rv2389c, Rv0867c, TB18.2, Rv2099c, Rv1733c, *M.tb* PPD, PHA and ESAT-6/CFP-10 and the presence, absence or level of at least one host marker in the sample is detected, the host marker being selected from EGF, TGF-α, TNF-α, VEGF, RANTES, IL-12(p40), IL-12(p70), IL-10, IP-10, IFN-α2, fractalkine, IFN-γ, IL-13, IL-1Ra, IL-3, IL-4, IL-5, MIP-1α, ENA-78, BCA-1, TARC, X6-Ckine, eotaxin, eotaxin-2, SCF, APOA-1, APOE, HPALBN, HCF, Serum amyloid protein A (SAA), C-reactive protein (CRP), serum amyloid protein P (SAP), TIMP-1, MIP-1β, IL-6, GM-CSF, IL-1α, MMP-9, MMP-2, MCP-1, TRAIL, IL-15, IL-17F, IL-22, TNF-β, MCP-2 and MCP-4. The absence, presence or level of the host marker(s) indicates that the subject has TB disease. As the method can distinguish between latent *Mycobacterium tuberculosis* infection (LTBI) and active TB disease, it is particularly suitable for use in populations or areas where there is high LTBI, but also in low and intermediate TB prevalence areas.

Active tuberculosis (referred to herein as TB disease) is the disease state where a sample from a subject is smear microscopy or culture positive for *M. tuberculosis*, or *M. tuberculosis* is detectable by a nucleic acid amplification test, and the subject has clinical and radiological features of active disease (constitutional symptoms are often present). LTBI is where potentially viable *M.tb* is present in the sample (usually assumed from positive tests for immune reactivity against *M.tb*) but the subject is asymptomatic, and without clinico-radiological features of active disease.

The sample can be whole blood or blood cells, or fluid from the pleural space, the pericardial space, abdominal cavity or sub-arachnoid space. More preferably, the sample is whole blood or blood cells, either diluted or undiluted.

The method may also comprise the step of detecting one or more host markers in the sample before it is stimulated with the antigen(s). For example, the detection of one or more of non-antigen specific CRP, SAA, SAA, TIMP-1, BCA-1, ENA-78, IL-1α, MMP-2, IFN-α2 and fractalkine in the unstimulated sample, in addition to the detection of one or more of the antigen-specific host markers described above, can be used to diagnose TB disease.

After the sample has been stimulated with the antigens and the levels of host markers in the stimulated sample have been determined, these can be compared to the levels of the same host marker(s) in a subject without TB disease, with or without latent *Mycobacterium tuberculosis* infection (LTBI). Alternatively, the levels of the host markers in subjects without TB disease can already have been determined and a cut-off level can have been determined for differentiating between TB disease and no TB disease. An indicator can be used to indicate whether the subject has TB disease or not based on whether the level of the host marker is above or below the cut-off level. The indicator can be a chromatographic indicator or an ELISA assay or any other quantitative assay for host marker levels.

The method can be used to diagnose pulmonary or extrapulmonary TB disease. Extrapulmonary TB sites include the pleura (in tuberculosis pleurisy), the central nervous system and sub-arachnoid space (in meningitis), the lymphatic system peripheral lymph nodes, the genitourinary system (in urogenital tuberculosis), pericardial space, abdominal cavity, and bones and joints (in Pott's disease).

In one embodiment of the invention, antigens can be coated into blood collection tubes or containers. After phlebotomy, tubes containing the blood samples can be stored at room temperature (even in Sub-Sahara Africa) for several (up to 12) hours before incubation at 37° C. in an incubator without $CO_2$ or humidification. After culture, preferably overnight, a dipstick-like test membrane or strip test could be inserted into the supernatant to detect the target host markers and results could be read in about 10 to 20 minutes. The dipstick-like test membrane or strip test could include antibodies against the target host markers and a secondary reactant to indicate the binding of the host markers to the antibodies.

Although the method of the invention will only yield results a day after the subject's visit, it might prove cheaper and more suitable in remote settings than the GeneXpert and conventional *M.tb* culture which has been the gold standard for a long time, but yet unavailable in these resource-limited settings. Such a test would also be beneficial to individuals that have difficulty in providing satisfactory sputum samples for microbiological and other tests, such as children and individuals with extrapulmonary TB.

A kit can also be provided for performing the diagnostic method of the invention. The kit could include:
one or more antigens selected from Rv0081, Rv2032, Rv1737c, Rv2389c, Rv0867c, TB18.2, Rv2099c, Rv1733c, *M.tb* PPD, PHA and ESAT-6/CFP-10;
means for detecting, measuring or analyzing the absence, presence or level of at least one host marker in a sample from the subject which has been stimulated with the antigen(s), the host marker being selected from EGF, TGF-α, TNF-α, VEGF, RANTES, IL-12(p40), IL-12(p70), IL-10, IP-10, IFN-α2, fractalkine, IFN-γ, IL-13, IL-1Ra, IL-3, IL-4, IL-5, MIP-1α, ENA-78, BCA-1, TARC, X6-Ckine, eotaxin, eotaxin-2, SCF, APOA-1, APOE, HPALBN, HCF, Serum amyloid protein A (SAA), C-reactive protein (CRP), serum amyloid protein P (SAP), TIMP-1, MIP-1β, IL-6, GM-CSF, IL-1α, MMP-9, MMP-2, MCP-1, TRAIL, IL-15, IL-17F, IL-22, TNF-β, MCP-2 and MCP-4;
and/or a means for indicating whether the subject has TB disease or not. The means for detecting, measuring or analyzing the absence, presence or level of the host marker(s) may comprise a dip stick or test strip which includes a chromatographic indicator or an ELISA kit, or any other suitable measuring and indicating means.

The applicant has previously shown that the detection of host markers other than IFN-γ in *M.tb*-specific antigen-stimulated whole blood cell cultures might be a useful approach for discriminating between LTBI and active TB disease[24]. 118 different *M.tb* infection phase-dependent antigens were evaluated using a diluted whole blood assay to identify possible candidates for use in diagnosing TB disease, as determined by IFN-γ measurement. Many *M.tb* infection phase-dependent antigens with diagnostic potential were identified. However, none of these antigens sufficed for diagnosis of TB disease with an accuracy of 100%, and no such high accuracy was obtained even when antigens were used in combinations[24].

The levels of alternative host markers were therefore evaluated in whole blood culture supernatants, prior to and after stimulation with *M.tb* infection phase-dependent antigens, for the diagnosis of TB disease. Blood cells were stimulated with two resuscitation promoting factors (rpfs) (Rv0867c and Rv2389c), four DosR regulon-encoded antigens (Rv2032, Rv0081, Rv2099c, Rv1733c, Rv1737c), a novel *M.tb* specific antigen (TB18.2), two classical *M.tb* antigens (*M.tb* PPD and ESAT-6/CFP-10 fusion protein), a positive control (PHA) and an unstimulated (negative) control. The antigen-stimulated or unstimulated samples were cultured using both a long-term (7 day) whole blood assay (WBA), an in-house short-term overnight WBA and a QFT-IT overnight WBA. Supernatants were harvested, aliquoted and the levels of the host markers were evaluated by the Luminex technology. The results show that different *M.tb* infection phase-dependent antigens elicit the production of different host markers by blood cells, some with diagnostic potential.

Rv0081-specific levels of IL-12(p40), IP-10, IL-10, TNF-α, IL-6, MCP-1, MIP-1β, TNF-α, ENA-78, X6-Ckine, Rv2029c-specific levels of ENA-78 and X6-Ckine, TB18.2-specific levels of GM-CSF and IL-15, and the unstimulated levels of CRP, SAP and TIMP-1 were the most promising diagnostic candidates, each ascertaining TB disease with an accuracy of 100%, 95% confidence interval for the area under the receiver operating characteristics plots (1.0 to 1.0).

The invention will now be described in more detail with reference to the following non-limiting examples.

Examples

Materials and Methods
Study Participants

Study participants were recruited from the Ravensmead/Uitsig community in the Western Cape Province of South Africa. The study population consisted of already diagnosed first time TB cases that were enrolled before the initiation of anti-TB therapy (n=10), and 20 participants that were suspected of having TB disease upon presentation with symptoms (including cough for >2 weeks), at the health care facility. All study participants underwent a thorough clinical workup including chest x-rays, HIV testing using a rapid test (Abott, Germany) and collection of samples for standard routine clinical investigations and the extra blood and sputum samples needed for research purposes. The sputum samples collected from all participants were sent to the research laboratory where they were cultured using Bactec MGIT method (BD Biosciences). Isolation of *M.tb* complex organisms was confirmed in all positive cultures by means of an *M.tb* complex specific PCR[3]. Participants were eligible for the study if they were ≥18 years old, had no previous history of TB, were not pregnant, were not involved in a drug or vaccine trial and if they had no other known chronic diseases like diabetes mellitus. All participants provided written informed consent for participation in the study including for HIV testing, storage and use of the samples for immunological biomarker discovery purposes. Ethical approval for the study was obtained from the Human Research Ethics Committee of the University of Stellenbosch (N10/08/274).

Pulmonary TB disease was confirmed in five of the 20 participants suspected of having TB, as well as all the 10 already known first-time TB cases. These 15 individuals constituted the "TB disease" group referred to herein. The "no TB disease" group was made up of the 15 remaining participants who had negative cultures and no other signs suggestive of active pulmonary TB or extra-pulmonary TB disease, including negative chest X rays. In the second part of the study, the same samples (as mentioned above) were collected and after the whole blood assays described below were performed, the levels of 73 host markers were evaluated. The 8 TB cases and 8 controls included in this second part of the study were patients suspected of having TB disease and diagnosed using the same criteria.

Whole Blood Culture Assays (WBA)

About 10 ml of whole blood was collected from all study participants into heparinized tubes for overnight and long term (7-day) WBAs and 3 ml for QFT-IT testing, directly into tubes provided by the manufacturer (Qiagen, Germany).

Recombinant proteins were obtained from Leiden University Medical Centre, The Netherlands (Rv2029c, Rv2032, Rv2389c, ESAT6/CFP10 fusion protein, Rv0081, Rv1733c) or from the Statens Serum Institute, Copenhagen, Denmark (TB18.2 and *M.tb* PPD). All antigens were reconstituted and evaluated at a final concentration of 10 μg/ml in an overnight and 7-day WBA as follows:

The 7-day WBA was performed as described in detail in Chegou et al. (2012)[15], the contents of which are specifically incorporated herein. Briefly, lyophilized antigens were reconstituted in sterile 1×PBS and diluted to a concentration of 20 μg/ml with RPMI 1640 containing L-glutamine (Sigma Aldrich, Steinheim, Germany). The diluted antigens (100 μl at 20 μg/ml) as well as the medium (unstimulated control), were then seeded into 96-well plates in triplicates after which plates were frozen at −80° C. until the day of WBA. On the day of WBA, pre-frozen antigen plates were allowed to thaw after which whole blood was diluted 1 in 5 in pre-warmed (37° C.) RPMI1640 medium containing glutamine, and then 100 μl of the diluted blood added into each well containing the antigens. The plate was then incubated at 37° C. until day 7 after which supernatants were harvested, aliquoted and frozen at −80° C. for testing using the Luminex technology as described below.

For the overnight WBA (an in-house assay developed by the applicant), the reconstituted antigens (in sterile 1×PBS) were diluted to a concentration of 100 μg/ml using sterile 1×PBS. Each diluted antigen (at 100 μg/ml) was then aliquoted in 100 μl amounts and then frozen at −80° C. in micro centrifuge tubes (Eppendorf Germany). On the day of WBA, an aliquot of each antigen (100 μl at 100 μg/ml) was thawed and added to 1 ml of undiluted whole blood in 24-well tissue culture plates (Corning Costar, Sigma). 100 μl of sterile 1×PBS was added to a single well of the 24-well plate for each participant and evaluated as the unstimulated control. After mixing, plates were incubated for 20 to 24 hours at 37° C. in a 5% $CO_2$ atmosphere. Supernatants were harvested, aliquoted and frozen at −80° C. until evaluated using the Luminex technology (described below).

The QFT-IT assay was performed according to the manufacturer's instructions as previously described[23]. Briefly, after overnight incubation of the blood in the QFT-IT tubes, supernatants were harvested, aliquoted and frozen at −80° C. Aliquots of supernatants from all participants were used for IFN-γ ELISA using kits supplied by the manufacturer (Qiagen, Germany). Other aliquots were used for the Luminex assay (described below).

Luminex Multiplex Immunoassay

In the first part of the study, a total of 26 host markers, namely: epithermal growth factor (EGF), fractalkine, IP-10, monocyte chemotactic protein (MCP)-1, macrophage inflammatory protein (MIP)-1α, MIP-1β, soluble CD40 ligand (sCD40L), TGF-α, TNF-α, VEGF, matrix metalloproteinase (MMP)-2, MMP-9, RANTES, C-reactive protein (CRP), serum amyloid protein A (SAA), Serum amyloid protein P (SAP), Interferon (IFN)-α2, IFN-γ, IL-1α, IL-12p40, IL-15, IL-17, IL-4, IL-10, IL-1β and IL-12p70, were evaluated in overnight, 7-day, and QFT-IT culture supernatants from all study participants, using customized Milliplex kits (Merck Millipore, St. Charles, Mo., USA). In the second part of the study, 73 analytes were examined, namely: EGF, eotaxin, granulocyte colony stimulating factor (G-CSF), granulocyte-monocyte colony stimulating factor (GM-CSF), IFN-α2, IFN-γ, IL-10, IL-12 (p40), IL-12 (p70), IL-13, IL-15, IL-17, IL-1ra, IL-1α, IL-1β, IL-2, IL-3, IL-4, IL-5, IL-6, IL-7, IL-8, IP-10, MCP-1, MIP-1α, MIP-1β, TNF-α, TNF-β, VEGF, 6-Ckine, B-cell attracting chemokine (BCA)-1, chemokine (c-c motif) ligand-27 (CTACK), CXCL5 (ENA-78), eotaxin-2, eotaxin-3, CCL1 (I-309), IL-16, IL-20, IL-21, IL-23, IL-28A, IL-33, leukemia inhibitory factor (LIF), MCP-2, MCP-4, MIP-1d, stem cell factor (SCF), SDF-1A+β, TARC, TPO, TRAIL, TSLP, IL-17E/IL-25, IL-17F, IL-22, IL-27, IL-31, matrix metalloproteinase (MMP)-2, MMP-9, tissue inhibitors of matrix metallo-proteinases (TIMMP)-1, TIMMP-2, TIMMP-3, TIMMP-4, C-reactive protein (CRP), serum amyloid protein A (SAA), serum amyloid protein P (SAP), and mediators of the complement pathway: Complement C3, Complement factor H, A-2-macroglobulin, Apo A1, Apo CIII, Apo E, Preabumin. All assays were performed on the Bio Plex platform (Bio Plex™, Bio Rad Laboratories) according to the instructions of the kit manufacturer (Merck Millipore). Prior to assay, samples for the detection of CRP, SAA and SAP were diluted 1 in 8000 using the assay diluent provided in the kit, following optimization experiments. To enable the accurate detection of all the host markers evaluated, the overnight WBA and QFT-IT culture supernatants were diluted 1 in 2 using the kit serum matrix[23], whereas the 7-day WBA supernatants were tested neat (undiluted)[24]. Samples were evaluated in a blinded manner. All analyte levels in the quality control reagents provided by the kit manufacturer were within the expected ranges. The values obtained for all host markers were automatically corrected for the dilution by the software used for bead acquisition and analysis of median fluorescence intensity (Bio-Plex Manager™ Software, version 4.1.1).

Statistical Analysis

Comparison between groups (for example TB vs. no TB) was done using the Mann Whitney U test for non-parametric data analysis. The accuracy of all antigen-induced host markers for the diagnosis of TB disease was estimated by performing receiver operator characteristics (ROC) curve analysis. Optimal cut-off values were selected based on the maximum Youden's index or highest likelihood ratio. The predictive abilities of combinations of analytes for TB disease were investigated by performing best subsets general discriminant analysis (GDA), with leave-one-out cross validation[23]. Data were analysed using the Statistica software (Statsoft, Ohio, USA) and GraphPad prism, version 5.00 for Windows (GraphPad Software, San Diego, Calif., USA).

Results

Study Participants

Of the 30 participants enrolled into the first part of the study, 6 (25%) were males. The mean age of the study participants was 29.97±12.7 years. All the 15 study participants with TB disease had culture and $M.tb$-PCR-confirmed pulmonary TB. Of all the 27 participants in whom QFT-IT testing was done, 19(70.4%) were positive using the manufacturer's recommended cut-off value (≥0.35 IU/ml). The clinical and demographic characteristics of all study participants are shown in Table 1.

TABLE 1

Clinical and demographic characteristics of study participants

| | All | Pulmonary TB | No TB |
|---|---|---|---|
| Number of participants (n) | 30 | 15 | 15 |
| Mean age, years (range) | 29.97 (8-59) | 26 (8-56) | 33.5 (31-59) |
| Male/female ratio | 6/24 | 4/11 | 2/13 |
| HIV status (pos/negative) | 3/30 | 0/15 | 3/15 |
| Participants with QFT test | 27 | 13 | 14 |
| QFT positive, n (%) | 19 (70.4) | 12 (92.3) | 7 (50) |

Utility of Host Markers Detected in 7-Day Antigen-Stimulated Culture Supernatants in the Diagnosis of TB Disease Of the 26 host markers evaluated in the first part of the study, the levels of 10 (fractalkine, IFN-α2, MMP-2, MMP-9, SAA, IP-10, EGF, IFN-γ, MMP-2, MMP-9) were significantly different ($p<0.05$) or showed trends ($0.05<p≤0.09$) between the TB cases and controls (50% of whom were infected with $M.tb$), either in the 7-day unstimulated supernatants or following 7-day stimulation with at least one of the four antigens evaluated.

The unstimulated levels of fractalkine and SAA were significantly higher in TB cases, whereas the unstimulated levels of IFN-α2 and MMP-2 were higher in the non TB cases. The unstimulated levels of EGF and IP-10 showed a trend towards significance ($0.05≤p≤0.09$) (Table 2).

When the antigen-specific responses were calculated by subtraction of the unstimulated marker levels from the levels obtained after stimulation with the respective antigens, ESAT-6/CFP-10-specific levels of EGF, IP-10 and MMP-9 were significantly higher ($p<0.05$) in TB cases, whereas ESAT-6/CFP-10-specific levels of IP-10 and IFN-γ showed a trend towards significance (higher in the TB cases) (Table 2). Following stimulation with Rv2029c, only MMP-9 responses were significantly different between the TB and non TB cases (higher in the TB cases), with the levels of IL-17 showing a trend towards significance (higher in the non-TB cases) (Table 2). Similarly, Rv2389c elicited the production of higher levels of MMP-9 and EGF in the TB cases, with Rv2389c-specific levels of MMP-2 showing a trend towards significance (higher in the TB cases). Only EGF levels were significantly different between the TB cases and controls (higher in TB cases) following stimulation with Rv2032 (Table 2, FIG. 1).

When the diagnostic accuracy of the markers obtained in supernatants after 7-day stimulation of whole blood with the antigens was evaluated by ROC curve analysis, the area under the ROC curve (AUC) was above 0.70 for ESAT-6/CFP-10 specific levels of EGF, IP-10, and MMP-9, Rv2029c-specific levels of MMP-9, Rv2389c-specific levels of EGF and MMP-9, and Rv2032-specific levels of EGF and unstimulated levels of fractalkine, IFN-α2, MMP-2 and SAA. Using cut-off values derived after ROC analysis, only the unstimulated levels of fractalkine and Rv2389c-specific MMP-9 ascertained TB disease with sensitivity above 90% (100% and 93%) and with specificities of 53% and 79%, respectively. ESAT-6/CFP-10 specific MMP-9 was the only marker that ascertained TB disease with both sensitivity and specificity ≥80% (Table 2).

Figure 2:
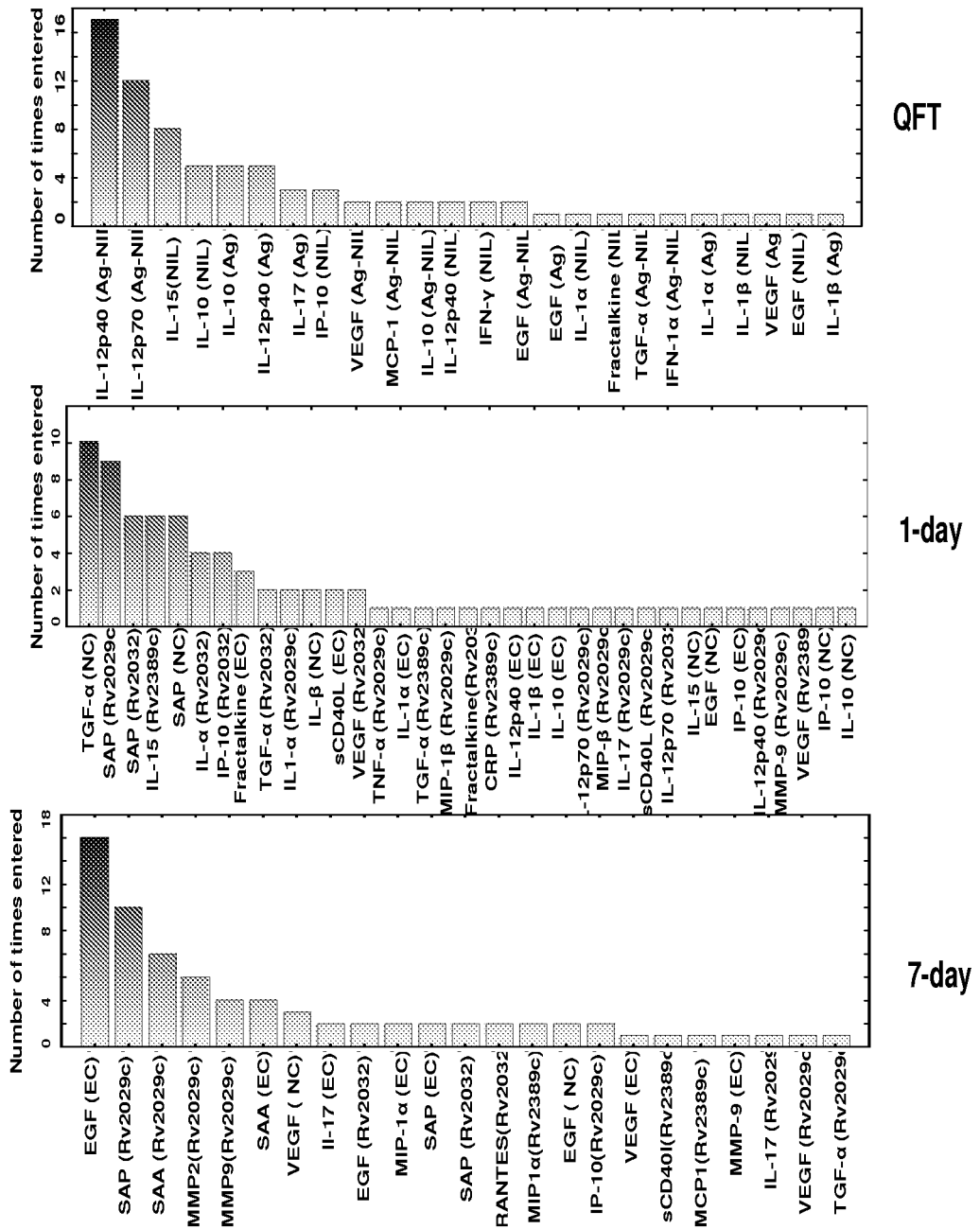
FIG. 2: Number of inclusions of antigen-induced markers into the top 20 models that most accurately discriminated between patient groups by general discriminant analysis in the three different WBA assays. The columns represent the number of times the analyte was included into the top-20 models. NC: unstimulated control, Ag: antigen, EC: ESAT-6/CFP-10. QFT=QFT-IT, 1-day=overnight (in-house) whole blood assay, 7-day=7-day whole blood culture assay.
Figure 3:
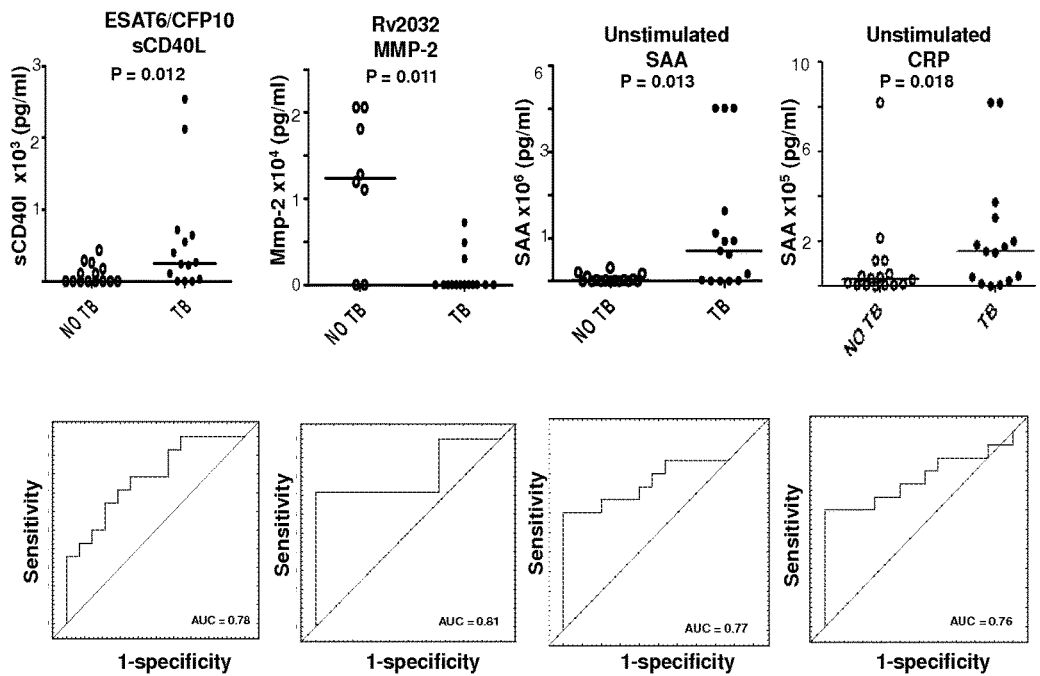
FIG. 3: Representative scatter-dot plots showing levels of analytes in the overnight (in-house) whole blood culture supernatants and ROC curves for accuracy in the diagnosis of TB disease. Error bars in the scatter dot plots represent the median analyte levels. Some analytes with AUC≥0.76 are shown.

When the accuracy of combinations of markers was assessed by general discriminant analysis (GDA), optimal prediction of TB disease was achieved if markers were used in combinations of four. The most accurate prediction model comprised ESAT-6/CFP-10-specific EGF, ESAT-6/CFP-10-specific IL-17, Rv2389c-specific MMP-2 and unstimulated levels of VEGF; accurately classifying 87% of the TB cases and 86% of the non-TB cases after leave-one-out cross validation (Table 3). The most frequently occurring analytes in the 20 most accurate predictive models included ESAT-6/CFP-10 specific EGF, Rv2029c-specific SAP and Rv2029c-specific SAA (FIG. 2).

TABLE 2

Median levels (and ranges in parenthesis) of analytes detected in 7-day whole blood culture supernatants and accuracy in the diagnosis of TB disease.

| Antigen | Marker | TB | No TB | P-value | AUC % (95% CI) | Sensitivity % (95% CI) | Specificity % (95% CI) | Cut off value |
|---|---|---|---|---|---|---|---|---|
| ESAT6/CFP10 | EGF | 6.2 (0-12.89) | 0 (−2.3-4.8) | 0.003 | 80 (64-96) | 67 (38-88) | 80 (52-96) | 1.470 |
| ESAT6/CFP10 | IP-10 | 4015 (334-15943) | 1664 (0-9999) | 0.05 | 71 (53-90) | 73 (45-92) | 53 (27-79) | 1675 |
| ESAT6/CFP10 | MMP-9 | 77644 33259-205268 | 32611 (0-272113) | 0.006 | 82 (62-98) | 87 (60-98) | 80 (52-96) | 61832 |
| Rv2029c | MMP-9 | 83925 23153-234362 | 36556 (0-120001) | 0.014 | 77 (60-94) | 71 (42-92) | 60 (52-96) | 68176 |
| Rv2032 | EGF | 8.1 (0-25) | 5.3 (0-22.8) | 0.023 | 74 (56-92) | 67 (38-88) | 60 (60-84) | 4.260 |
| Rv2389c | EGF | 9.9 (0-26.5) | 1 (0-37) | 0.023 | 74 (56-94) | 73 (45-92) | 79 (49-95) | 8.730 |
| Rv2389c | MMP-9 | 69513 37074-960090 | 17719 (382-83527) | 0.0004 | 89 (76-100) | 93 (68-100) | 79 (49-95) | 50285 |
| Unstimulated | fractalkine | 33 (15-33) | 3.5 (2.2-432) | 0.05 | 71 (51-91) | 100 (78-100) | 53 (27-79) | 9.455 |
| Unstimulated | IFN-α2 | 2.3 (2.2-5.9) | 10 (2.2-19) | 0.038 | 72 (53-91) | 87 (60-98) | 60 (32-83) | 7.445 |
| Unstimulated | MMP-2 | 251 (112-40475) | 5805 (112-66578) | 0.023 | 74 (55-93) | 80 (52-96) | 73 (45-92) | 4359 |
| Unstimulated | SAA | 22661 (0-90178) | 4736 (560-34274) | 0.041 | 72 (53-92) | 73 (45-92) | 69 (39-91) | 630.5 |

All analyte levels are in pg/ml except for SAA (ng/ml).
P-values were calculated using the Mann Whitney U test.
Cut-off values, sensitivity and specificity were selected at the maximum Youden's index.
AUC = Area under the receiver operator characteristics curve.
95% CI = 95% confidence interval

TABLE 3

General discriminant analysis (GDA): Accuracy of 4-analyte models generated for markers detected in 7-day whole blood culture supernatants in the diagnosis of TB disease

| Host marker model (7-day WBA) | Resubstitution Classification Matrix | | | Leave-one-out Cross validation | | Wilks lambda | f | P-value |
|---|---|---|---|---|---|---|---|---|
| | % TB cases | % HHCs | Total % | % TB cases | % HHCs | | | |
| EGF(ESAT6/CFP10), VEGF (Rv2032), MCP-1(Rv2389c), MMP-9(Rv2389c) | 93 | 100 | 97 | 93 | 100 | 0.862 | 3.8 | 0.062 |
| EGF(ESAT6/CFP10), VEGF (Rv2032), sCD40L(Rv2389c), MMP-9(Rv2389c) | 93 | 100 | 97 | 87 | 100 | 0.939 | 1.6 | 0.22 |
| EGF(ESAT6/CFP10), VEGF (Rv2032), MMP-9(Rv2389c), SAP(Rv2029c) | 100 | 100 | 100 | 87 | 100 | 0.975 | 0.57 | 0.459 |
| EGF(ESAT6/CFP10), VEGF (Rv2032), MCP-1(Rv2032), MMP-9(Rv2389c) | 93 | 100 | 97 | 93 | 100 | 0.866 | 3.7 | 0.066 |
| EGF(ESAT6/CFP10), VEGF (Rv2032), IP-10(Unstimulated), MMP-9(Rv2389c) | 93 | 100 | 97 | 87 | 100 | 0.851 | 4.2 | 0.052 |
| EGF(ESAT6/CFP10), VEGF (Rv2032), Rantes(Unstimulated), MMP-9(Rv2389c) | 93 | 100 | 97 | 87 | 100 | 0.833 | 4.8 | 0.038 |
| EGF(ESAT6/CFP10), VEGF (Rv2032), MMP-2(ESAT6/CFP10), MMP-9(Rv2389c) | 93 | 100 | 97 | 93 | 100 | 0.972 | 0.7 | 0.420 |
| EGF(ESAT6/CFP10), VEGF (Rv2032), IL-1beta(Rv2029c), MMP-9(Rv2389c) | 100 | 100 | 100 | 100 | 100 | 0.996 | 0.1 | 0.768 |
| EGF(ESAT6/CFP10), VEGF (Rv2032), MMP-9(Rv2389c), MCP-1(ESAT6/CFP10) | 93 | 100 | 97 | 93 | 93 | 0.942 | 1.5 | 0.239 |
| EGF(ESAT6/CFP10), VEGF (Rv2032), MMP-9(Rv2389c), Fractalkine(Unstimulated) | 93 | 100 | 97 | 93 | 93 | 0.866 | 3.7 | 0.066 |
| EGF(ESAT6/CFP10), VEGF (Rv2032), MMP-9(Rv2389c), IL-12p40(Rv2029c) | 93 | 100 | 97 | 93 | 100 | 0.966 | 0.8 | 0.384 |
| EGF(ESAT6/CFP10), VEGF (Rv2032), MMP-9(Rv2389c), MIP-1α(Rv2029c) | 100 | 100 | 100 | 86 | 100 | 0.995 | 0.1 | 0.757 |
| EGF(ESAT6/CFP10), VEGF (Rv2032), MMP-9(Rv2389c), SAP(Rv2032) | 100 | 100 | 100 | 87 | 100 | 0.988 | 0.3 | 0.596 |
| EGF(ESAT6/CFP10), VEGF (Rv2032), MMP-9(Rv2389c), VEGF(Unstimulated) | 93 | 100 | 97 | 80 | 100 | 0.871 | 3.4 | 0.072 |
| EGF(ESAT6/CFP10), VEGF (Rv2032), MMP-9(Rv2389c), TNF-α(Rv2029c) | 93 | 100 | 97 | 93 | 100 | 0.994 | 0.1 | 0.729 |
| EGF(ESAT6/CFP10), VEGF (Rv2032), MMP-9(Rv2389c), IL-12p40(Rv2032) | 100 | 100 | 100 | 80 | 100 | 0.980 | 0.5 | 0.492 |
| EGF(ESAT6/CFP10), VEGF (Rv2032), MMP-9(Rv2389c), CRP(Unstimulated) | 93 | 100 | 97 | 80 | 100 | 0.913 | 0.2 | 0.145 |
| EGF(ESAT6/CFP10), VEGF (Rv2032), MMP-9(Rv2389c), EGF(Rv2389c) | 93 | 100 | 97 | 80 | 100 | 0.912 | 2.3 | 0.143 |
| EGF(ESAT6/CFP10), VEGF (Rv2032), MMP-9(Rv2389c), MIP-1β(Rv2389c) | 100 | 100 | 100 | 93 | 100 | 0.998 | 0.04 | 0.832 |
| EGF(ESAT6/CFP10), VEGF (Rv2032), MMP-9(Rv2389c), IL-1α(Rv2032), | 100 | 100 | 100 | 80 | 100 | 0.996 | 0.08 | 0.786 |

Utility of Host Markers Detected in Overnight Culture Supernatants for Diagnosing TB Of the 26 host markers evaluated in the first part of the study, the unstimulated or antigen-specific levels of 9 (MMP-2, sCD40L, IP-10, IFN-γ, IL-1β, TNF-α, SAA, SAP, and CRP) showed significant differences or trends between the TB cases and controls. Unstimulated CRP and SAA levels were significantly higher in the TB cases. ESAT-6/CFP-10-specific levels of IP-10, sCD40L, TNF-α, IFN-γ, and SAP were significantly higher in TB cases. Similarly, Rv2389c-specific levels of SAP and CRP, and Rv2032-specific levels of SAP were higher in the TB cases, whereas Rv2032-specific MMP-2 was higher in the non TB cases (Table 3). When the diagnostic accuracy of the markers obtained after overnight culture was assessed by ROC curve analysis, all the markers that showed significant differences between groups ascertained TB disease with AUC>0.70 (range, 0.71 to 0.83). ESAT-6/CFP-10-specific IP-10 and IFN-γ, Rv2029c-specific IL-1β, Rv2032-specific MMP-2 all diagnosed TB disease with sensitivity ≥93%, but specificity was low for some markers (e.g. 67% for ESAT-6/CFP-10-specific IP-10). Contrarily, unstimulated CRP levels diagnosed TB with low sensitivity (60%) but with very high specificity (100%) (Table 4).

When the GDA procedure was applied to the markers detected in the overnight culture supernatants, optimal prediction of TB or no TB disease was achieved if markers were used in combinations of four. The most accurate 4-analyte model (Rv2029c-specific TNF-α+Rv2032-specific IFN-α2+Rv2032-specific SAP+Rv2389c-specific IL-15) accurately classified 92% of the TB cases and 85% of non TB cases after leave-one-out cross validation (Table 5). The most frequently occurring analytes in the top-20 predictive models included unstimulated TGF-α and Rv2029c-specific SAP (FIG. 2).

TABLE 4

Median levels (and ranges in parenthesis) of analytes detected in overnight (in-house) whole blood culture supernatants and accuracy in the diagnosis of TB disease.

| Antigen | Marker | TB | No TB | P-value | AUC % (95% CI) | Sensitivity % (95% CI) | Specificity % (95% CI) | Cut off value |
|---|---|---|---|---|---|---|---|---|
| ESAT6/CFP10 | IP-10 | 16811 (8176-19512) | 1826 (0-19353) | 0.042 | 76 (52-93) | 93 (66-100) | 67 (38-88) | 4499 |
| ESAT6/CFP10 | sCD40L | 252 (0-2539) | 0 (0-435) | 0.012 | 78 (61-94) | 78 (49-95) | 60 (32-84) | 15.01 |
| ESAT6/CFP10 | IFN-γ | 339 (8-3578) | 8 (0-1558) | 0.047 | 72 (52-92) | 93 (66-100) | 67 (38-88) | 59.81 |
| ESAT6/CFP10 | TNF-α | 36.2 (3-169) | 3 (0-113) | 0.033 | 0.70 (50-89) | 93 (66-100) | 53 (27-79) | 4.5 |
| ESAT6/CFP10 | SAP | 4481 (0-22380) | 0 (0-17026) | 0.025 | 74 (56-93) | 86 (57-98) | 67 (38-88) | 8.650 |
| ESAT6/CFP1 | MCP-1 | 3871 (50-18041) | 778 (0-13626) | 0.085 | 65 (44-85) | 71 (42-92) | 60 (32-84) | 1529 |
| ESAT6/CFP1 | MIP-α | 183 (2-1116) | 53 (0-477) | 0.063 | 68 (48-87) | 64 (35-87) | 60 (32-84) | 84 |
| ESAT6/CFP1 | MIP-β | 1023 (13-3558) | 128 (4-2316) | 0.063 | 65 (44-86) | 79 (49-95) | 60 (32-84) | 232 |
| Rv2029c | IL-1α | 0 (0-18.64) | 0 (0-24) | 0.037 | 71 (51-90) | 100 (74-100) | 25 (7-52) | −3.260 |
| Rv2029c | IP-10 | 11858 (751-19281) | 3474 (0-18433) | 0.048 | 70 (50-89) | 67 (34-90) | 69 (41-89) | 6805 |
| Rv2032 | MMP-2 | 0 (0-7236) | 12379 (0-20606) | 0.011 | 83 (2-100) | 100 (78-100) | 75 (35-97) | 9147 |
| Rv2032 | SAP | 5529 (0-24063) | 0 (0-20031) | 0.023 | 75 (57-93) | 73 (45-92) | 73 (45-92) | 2842 |
| Rv2389c | CRP | 6317 (0-442665) | 12.3 (0-116862) | 0.050 | 72 (52-92) | 69 (39-91) | 67 (38-88) | 1922 |
| Rv2389c | SAP | 6509 (0-22648) | 0 (0-10267) | 0.032 | 74 (55-93) | 69 (39-91) | 60 (32-84) | 1216 |
| Unstimulated | SAA | 705597 (560-4000000) | 15641 (560-309939) | 0.013 | 76 (58-95) | 73 (45-92) | 56 (30-80) | 20389 |
| Unstimulated | CRP | 152210 (120-816000) | 30463 (170-816000) | 0.018 | 77 (50-89) | 60 (32-84) | 100 (63-100) | 130552 |

All analyte levels are in pg/ml except for CRP, SAA and SAP (ng/ml).
P-values were calculated using the Mann Whitney U test.
Cut-off values, sensitivity and specificity were selected at the maximum Youden's index.
AUC = Area under the receiver operator characteristics curve.
95% CI = 95% confidence interval

TABLE 5

General discriminant analysis (GDA): Accuracy of 4-analyte models generated for markers detected in overnight (in-house) whole blood culture supernatants in the diagnosis of TB disease

| Host marker model | Resubstitution Classification Matrix | | | Leave-one-out Cross validation | | Wilks lambda | f | P-value |
|---|---|---|---|---|---|---|---|---|
| | % TB cases | % HHCs | Total % | % TB cases | % HHCs | | | |
| TNF-α(Rv2029c), IFN-α2(Rv2032), SAP(Rv2032), IL-15(Rv2389c) | 100 | 85 | 92 | 92 | 85 | 0.799 | 5.0 | 0.037 |
| SAP(Rv2029c), TGF- α(Rv2032), SAP(Unstimulated), TGF- α(Unstimulated) | 92 | 79 | 85 | 92 | 64 | 0.949 | 1.1 | 0.302 |
| IL-1 α(ESAT6/CFP10), SAP(Rv2029c), TGF- α(Rv2389c), SAP(Unstimulated) | 100 | 79 | 88 | 92 | 79 | 0.909 | 2.1 | 0.163 |
| fractalkine(ESAT6/CFP10), SAP(Rv2029c), TGF- α(Unstimulated), SAP(Unstimulated) | 92 | 71 | 80 | 92 | 71 | 0.986 | 0.3 | 0.602 |
| MIP-1β(Rv2029c), IFN-α2(Rv2032), SAP(Rv2032), IL-15(Rv2389c) | 100 | 85 | 92 | 92 | 77 | 0.814 | 4.6 | 0.045 |
| IL-1 α(Rv2029c), SAP(Rv2029c), IL-15(Rv2389c), IL-1 α(Unstimulated) | 92 | 71 | 81 | 75 | 64 | 0.493 | 21.6 | 0.000 |
| SAP(Rv2029c), fractalkine(Rv2032), TGF- α(Unstimulated), SAP(Unstimulated) | 100 | 86 | 92 | 83 | 71 | 0.910 | 2.1 | 0.166 |
| sCD40L(ESAT-6/CFP-10), IL-1 α (Rv2029c), TGF- α (Rv2032), CRP(Rv2389c) | 92 | 92 | 92 | 92 | 92 | 0.623 | 12.1 | 0.002 |
| IL-12p40(ESAT-6/CFP-10), IP-10(Rv2032), VEGF(Rv2032), TGF- α (Unstimulated) | 64 | 54 | 59 | 64 | 54 | 0.578 | 16.0 | 0.000 |
| fractalkine(ESAT-6/CFP-10), IL-1β(ESAT-6/CFP-10), SAP(Rv2029c), TGF- α (Unstimulated) | 94 | 64 | 77 | 92 | 57 | 0.451 | 25.5 | 0.000 |
| fractalkine(ESAT-6/CFP-10), IL-10(ESAT-6/CFP-10), SAP(Rv2029c), TGF- α (Unstimulated) | 100 | 64 | 81 | 100 | 57 | 0.522 | 19.2 | 0.000 |
| IL-12p70(Rv2029c), IP-10(Rv2032), VEGF(Rv2032), TGF-α (Unstimulated) | 92 | 36 | 62 | 58 | 29 | 0.632 | 12.2 | 0.002 |
| MIP-1 α(Rv2029c), IFN- α 2(Rv2032), SAP(Rv2032), IL-15(Rv2389c) | 100 | 77 | 88 | 92 | 77 | 0.862 | 3.2 | 0.089 |
| sCD40L(ESAT-6/CFP-10), IL-17(Rv2029c), SAP(Rv2032), IL-15(Rv2389c) | 100 | 85 | 92 | 92 | 85 | 0.504 | 19.6 | 0.000 |
| sCD40L(Rv2029c), IL-12p70(Rv2032), SAP(Rv2032), IL-15(Unstimulated) | 100 | 86 | 92 | 100 | 79 | 0.376 | 34.8 | 0.000 |
| SAP(Rv2029c), EGF(Unstimulated), TGF- α (Unstimulated), SAP(Unstimulated) | 100 | 67 | 81 | 92 | 67 | 0.965 | 0.8 | 0.386 |
| IP-10(ESAT-6/CFP-10), IL-12p40(Rv2029c), IP-10(Rv2032), TGF- α (Unstimulated) | 100 | 85 | 92 | 83 | 85 | 0.795 | 5.1 | 0.035 |
| MMP-9(Rv2029c), IFN- α 2(Rv2032), SAP(Rv2032), IL-15(Rv2389c) | 92 | 100 | 94 | 92 | 100 | 0.752 | 4.3 | 0.059 |
| IP-10(Rv2032), VEGF(Rv2389c), IP-10(Unstimulated), IL-10(Unstimulated) | 77 | 69 | 73 | 62 | 62 | 0.825 | 4.5 | 0.047 |
| SAP(Rv2029c), IL-1 α (Unstimulated), TGF- α (Unstimulated), SAP(Unstimulated) | 92 | 73 | 91 | 92 | 73 | 0.985 | 0.3 | 0.570 |

Figure 4:
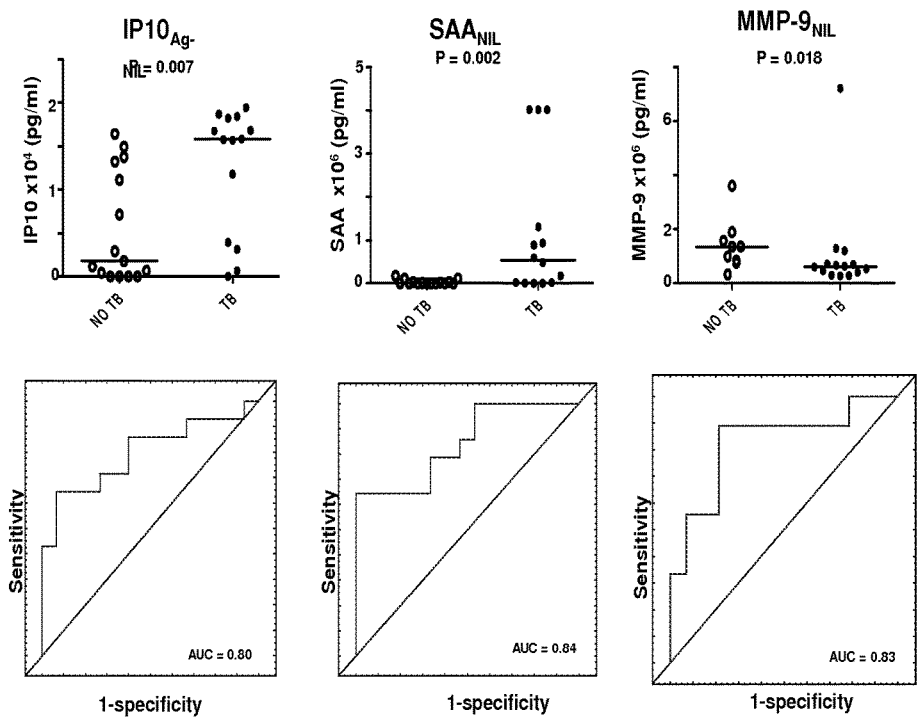
FIG. 4: Representative scatter-dot plots showing levels of analytes in the QFT-IT whole blood culture supernatants and ROC curves for accuracy in the diagnosis of TB disease. Error bars in the scatter dot plots represent the median analyte levels. Some analytes with AUC≥0.82 are shown.

Utility of Host Markers Detected in QFT-IT Supernatants in the Diagnosis of TB Disease The unstimulated or antigen stimulated levels of 11 of the 26 markers evaluated in the first part of the study (MCP-1, MIP-1l, VEGF, IP-10, IL-10, IL-1β, TGF-α CRP, SAA, SAP and MMP-9) showed significant differences or trends when evaluated in QFT-IT supernatants, with most of the discriminatory markers being detected in unstimulated supernatants. The unstimulated levels of 7 markers (MCP-1, MIP-1β, VEGF, IL-10, IL-1β, TGF-α, CRP and MMP-9) were significantly higher in the non-TB cases while the unstimulated levels of CRP, SAA, SAP and IP-10 were significantly higher in the TB cases. The antigen-specific levels of MCP-1 and IP-10 were significantly higher in the TB cases, with the levels of IFN-γ showing a trend (higher in TB cases) (Table 6, FIG. 4). When the diagnostic accuracy of the data obtained from QFT-IT supernatants was assessed by ROC curve analysis, AUC was ≥0.70 for all the markers showing significant differences between the TB cases and non-cases, including unstimulated MCP-1, MIP-1β, VEGF, IL-10, IL-1β, CRP, MMP-9, SAA, CRP and SAP (range 0.72-0.84). When the data was analysed by GDA, eight of the 20 most accurate 4-analyte prediction models accurately classified 100% of the TB cases and up to 89% of the non-TB cases after leave-one-out cross validation (Table 7).

The most frequently occurring analytes in the top 20 models included the antigen-specific levels of IL-12p70, IL-12p40, and unstimulated IL-15 (FIG. 2).

Identification of Novel Antigen-Specific and Unstimulated Host Markers in Overnight Culture Supernatants for the Diagnosis of TB Disease To investigate novel diagnostic candidates, the levels of 73 host markers were evaluated in overnight culture supernatants from 8 TB cases and 8 controls. This was done in unstimulated supernatants and in supernatants stimulated with 7 antigens including ESAT-6/CFP-10, *M.tb* PPD, PHA, Rv0081, Rv2029c, Rv1733c and TB18.2. The 73 host markers evaluated include cytokines, chemokines and growth factors namely: EGF, eotaxin, G-CSF, GM-CSF, IFN-α2, IFN-γ, IL-10, IL-12 (p40), IL-12 (p70), IL-13, IL-15, IL-17, IL-1ra, IL-1α, IL-1β, IL-2, IL-3, IL-4, IL-5, IL-6, IL-7, IL-8, IP-10, MCP-1, MIP-1α, MIP-1β, TNF-α, TNF-β, VEGF, 6-Ckine, BCA-1, CTACK, ENA-78, eotaxin-2, eotaxin-3, I-309, IL-16, IL-20, IL-21, IL-23, IL-28A, IL-33, LIF, MCP-2, MCP-4, MIP-1d, SCF, SDF-1A+β, TARC, TPO, TRAIL, TSLP, IL-17E/IL-25, IL-17F, IL-22, IL-27, IL-31, matrix metallo-proteinases and their tissue inhibitors namely: MMP-2 and MMP-9, TIMMP-1, TIMMP-2, TIMMP-3, TIMMP-4, acute phase proteins: CRP, SAA, SAP, and mediators of the complement pathway: Complement C3, Complement factor H, A-2-macroglobulin, Apo A1, Apo CIII, Apo E, Preabumin.

TABLE 6

Median levels (and ranges in parenthesis) of analytes detected in QFT-IT overnight whole blood culture supernatants and accuracy in the diagnosis of TB disease.

| Markers | TB cases (n=) | Non TB cases (n=) | P-value | AUC (95% CI) | Sensitivity, % (95% CI) | Specificity, % (95% CI) | Cut off value |
|---|---|---|---|---|---|---|---|
| $VEGF_{Ag}$ | 100 (2-290) | 120 (2-352) | 0.085 | 67 (47-87) | 79 (49-95) | 60 (32-84) | 117 |
| $CRP_{Ag}$ | 188210 (3411-816000) | 12918 (120-332914) | 0.009 | 80 (62-95) | 64 (49-95) | 87 (27-78) | 72307 |
| $SAA_{Ag}$ | 579939 (560-4000000) | 1115 (560-222320) | 0.004 | 82 (66-98) | 79 (49-95) | 73 (45-92) | 22752 |
| $SAP_{Ag}$ | 48247 (24799-74998) | 35242 (560-69282) | 0.034 | 73 (54-93) | 79 (49-95) | 80 (52-96) | 41205 |
| $MMP-9_{Ag}$ | 738806 (354239-700362629) | 1435154 (278743-2444144) | 0.073 | 0.72 (49-95) | 71 (42-92) | 67 (30-93) | 935846 |
| $IP-10_{Ag-Nil}$ | 15799 (0-19426) | 1773 (0-16430) | 0.007 | 80 (65-97) | 64 (57-98) | 93 (32-84) | 15696 |
| $MCP-1_{Ag-Nil}$ | 388 (0-7881) | 0 (0-12922) | 0.047 | 73 (52-91) | 79 (49-95) | 67 (38-88) | -732 |
| $IFN-\gamma_{Ag-Nil}$ | 272 (31-2458) | 81 (0-1662) | 0.092 | 66 (46-86) | 71 (24-92) | 60 (32-84) | 126 |
| $MCP-1_{Nil}$ | 9969 (1909-18125) | 14912 (4368-20001) | 0.015 | 77 (59-94) | 60 (66-100) | 93 (32-84) | 14651 |
| $MIP-1\alpha_{Nil}$ | 1188 (71-4203) | 2130 (617-4920) | 0.093 | 69 (48-89) | 64 (35-87) | 73 (45-92) | 1235 |
| $MIP-1\beta_{Nil}$ | 1096 (74-2258) | 1792 (548-3190) | 0.017 | 76 (59-93) | 73 (42-92) | 64 (32-84) | 1334 |
| $TGF-\alpha_{Nil}$ | 8 (2-39) | 30 (2-144) | 0.047 | 70 (50-90) | 86 (57-98) | 60 (32-83) | 24 |
| $VEGF_{Nil}$ | 31 (2-626) | 285 (2-727) | 0.041 | 73 (51-91) | 60 (49-95) | 79 (32-84) | 216 |
| $IL-10_{Nil}$ | 8 (2-51) | 4 (2-86) | 0.032 | 74 (55-92) | 80 (35-87) | 64 (52-96) | 11 |
| $IL-1\beta_{Nil}$ | 108 (2-365) | 33 (17-1957) | 0.050 | 72 (53-90) | 67 (35-87) | 84 (38-88) | 254 |
| $CRP_{Nil}$ | 457028 (2831-816000) | 35080 (157-816000) | 0.032 | 78 (55-92) | 64 (42-91) | 80 (32-84) | 66232 |
| $SAA_{Nil}$ | 1979000 (943-4160000) | 1821 (560-173709) | 0.002 | 84 (70-99) | 64 (49-95) | 100 (38-88) | 176199 |
| $SAP_{Nil}$ | 44639 (23918-56777) | 32733 (22470-79572) | 0.026 | 76 (55-94) | 79 (49-95) | 73 (45-92) | 38751 |
| $MMP-9_{Nil}$ | 617975 275049-720100 | 1347000 (331645-360500) | 0.018 | 83 (60-100) | 89 (49-95) | 79 (51-100) | 766037 |

All analyte levels are in pg/ml except for CRP, SAA and SAP (ng/ml).
P-values were calculated using the Mann Whitney U test.
Cut-off values, sensitivity and specificity were selected at the maximum Youden's index.
AUC = Area under the receiver operator characteristics curve.
95% CI = 95% confidence interval.
Nil = unstimulated marker levels, Ag = levels detected in antigen stimulated supernatants, Ag-N = Antigen specific marker levels obtained after subtraction of Nil responses.

TABLE 7

General discriminant analysis (GDA): Accuracy of 4-analyte models generated for markers detected in QFT-IT whole blood culture supernatants in the diagnosis of TB disease.

| | Resubstitution Classification Matrix | | | Leave-one-out Cross validation | | | | |
|---|---|---|---|---|---|---|---|---|
| Host marker model | % TB cases | % HHCs | Total % | % TB cases | % HHCs | Wilks lambda | f | P-value |
| $IL-12p40_{Ag-Nil}$, $IL-12p70_{Ag-Nil}$, $IL-15_{Nil}$, $IL-10_{Nil}$ | 100 | 100 | 100 | 100 | 89 | 0.850 | 3.16 | 0.092 |
| $EGF_{Ag}$, $IL-12p40_{Ag-Nil}$, $IL-12p70_{Ag-Nil}$, $IL-15_{Nil}$ | 100 | 100 | 100 | 100 | 89 | 0.844 | 3.32 | 0.084 |
| $IL-12p40_{Ag-Nil}$, $IL-12p70_{Ag-Nil}$, $IL-15_{Nil}$, $IL-1\alpha_{Nil}$ | 100 | 89 | 96 | 100 | 89 | 0.601 | 11.9 | 0.002 |
| $IL-17_{Ag}$, $VEGF_{Ag-Nil}$, $fractalkine_{Nil}$, $IP-10_{Nil}$ | 100 | 100 | 100 | 100 | 89 | 0.433 | 23.5 | 0.000 |
| $IL-10_{Ag}$, $IL-12p40_{Ag-Nil}$, $IL-12p70_{Ag-Nil}$, $TGF-\alpha_{Ag-Nil}$ | 100 | 89 | 96 | 100 | 89 | 0.994 | 0.1 | 0.745 |
| $IL-17_{Ag}$, $MCP-1_{Ag-Nil}$, $VEGF_{Ag-Nil}$, $IP-10_{Nil}$ | 100 | 100 | 100 | 100 | 100 | 0.426 | 24.2 | 0.000 |
| $IL-12p40_{Ag}$, $IL-10_{Ag}$, $IL-10_{Ag-Nil}$, $IL-12p70_{Ag-Nil}$ | 100 | 100 | 100 | 100 | 89 | 0.812 | 4.2 | 0.056 |
| $IL-12p40_{Ag}$, $IL-12p40_{Nil}$, $IL-12p70_{Ag-Nil}$, $IFN-\gamma_{Nil}$ | 93 | 100 | 96 | 93 | 89 | 0.886 | 2.3 | 0.147 |
| $IL-12p40_{Ag}$, $IL-10_{Ag}$, $IL-12p70_{Ag-Nil}$, $IL-10_{Nil}$ | 100 | 100 | 100 | 100 | 89 | 0.794 | 4.7 | 0.045 |
| $IL-10_{Ag}$, $EGF_{Ag-Nil}$, $IFN-\alpha2_{Ag-Nil}$, $IL-12p70_{Ag-Nil}$ | 93 | 100 | 96 | 93 | 89 | 0.890 | 2.2 | 0.152 |
| $IL-12p40_{Ag}$, $IL-12p40_{Ag-Nil}$, $IL-12p70_{Nil}$, $IL-10_{Nil}$ | 100 | 100 | 100 | 93 | 100 | 0.929 | 1.4 | 0.256 |
| $IL-1\alpha_{Ag}$, $IL-12p40_{Ag-Nil}$, $IL-12p70_{Ag-Nil}$, $IL-15_{Nil}$ | 100 | 89 | 96 | 100 | 89 | 0.571 | 13.5 | 0.002 |
| $IL-1\alpha_{Nil}$, $IL-12p40_{Ag-Nil}$, $IL-12p70_{Ag-Nil}$, $IL-15_{Nil}$ | 100 | 100 | 100 | 100 | 89 | 0.667 | 9 | 0.008 |
| $IL-17Ag$, $EGF_{Ag-Nil}$, $IL-12p40_{Nil}$, $IP-10_{Nil}$ | 93 | 100 | 96 | 93 | 89 | 0.371 | 30.5 | 0.000 |
| $VEGF_{Ag}$, $IL-12p40_{Ag-Nil}$, $IL-12p70_{Ag-Nil}$, $IL-15_{Nil}$ | 100 | 89 | 96 | 100 | 89 | 0.661 | 9.2 | 0.007 |
| $IL-12p40_{Ag-Nil}$, $IL-12p70_{Ag-Nil}$, $IL-10_{Nil}$, $IFN-\gamma_{Nil}$ | 93 | 100 | 96 | 93 | 89 | 0.921 | 1.5 | 0.230 |
| $IL-10_{Ag}$, $MCP-1_{Ag-Nil}$, $IL-12p40_{Ag-Nil}$, $IL-12p70_{Ag-Nil}$ | 100 | 89 | 96 | 93 | 89 | 0.995 | 0.1 | 0.768 |
| $IL-12p40_{Ag-Nil}$, $IL-12p70_{Ag-Nil}$, $EGF_{Nil}$, $IL-15_{Nil}$ | 100 | 100 | 100 | 100 | 78 | 0.886 | 2.3 | 0.147 |
| $IL-12p40_{Ag-Nil}$, $IL-12p70_{Ag-Nil}$, $IL-1\beta_{Ag}$, $IL-15_{Nil}$ | 100 | 100 | 100 | 100 | 89 | 0.760 | 5.7 | 0.028 |
| $IL-12p40_{Ag}$, $IL-12p70_{Ag-Nil}$, $IL-10_{Nil}$, $IL-10_{Ag-Nil}$ | 100 | 100 | 100 | 100 | 89 | 0.786 | 4.9 | 0.040 |

Nil = unstimulated marker levels, Ag = levels detected in antigen stimulated supernatants, Ag-N = Antigen-specific biomarker levels obtained after subtraction of Nil responses.

Many of the markers obtained in unstimulated samples, as well as the antigen-specific responses, predicted TB disease with high accuracy. Many of the markers evaluated including Rv0081-specific IL-6, MCP-1, MIP-1β, TNF-α, ENA-78, X6-Ckine, Rv2029c-specific ENA-78, X6-Ckine, TB18.2-specific GM-CSF, IL-15, and unstimulated CRP, SAP and TIMP-1, ascertained TB disease with an accuracy of 100%. The P-values for discriminating between TB disease and no TB are shown in Table 8 and the AUC obtained after ROC curve analysis for each antigen-specific marker are shown in Table 9.

Out of the 73 analytes evaluated, the potentially most useful in unstimulated or antigen-specific supernatants include IFN-γ, IL-13, IL-1Ra, IL-5, MIP-1α, VEGF, ENA- 78, BCA, X6-Ckine, eotaxin-2, SCF, APOE, HPALBN, SAA, CRP, TIMP-1, MIP-1β. Furthermore, IL-6, GM-CSF, IL-1α, TNF-α, EGF, MMP-9, IFN-α2, MMP-2, MCP-1, TRAIL, IL-15 and SAP levels may also be useful.

Correlation Between Host Markers in the Overnight, 7-Day and QFT-IT Whole Blood Culture Assays The levels of the markers obtained after stimulation with each antigen (Rv2029c, Rv2032, Rv2389c and ESAT-6/CFP-10 or unstimulated) were compared between the different WBA types. Comparison between all three assay types was only possible with ESAT-6/CFP-10-specific and the unstimulated control responses as these were the only common conditions between all the assay types. Because of the relatively large number of markers evaluated in this study, only analytes that showed significant differences between the TB cases and non-cases in at least one of the assay types (in the first part of the study) were included in the analysis.

TABLE 8

Abilities of novel antigen-specific host markers to discriminate between individuals with pulmonary TB disease and no TB. The values under the different antigens represent the p-values for the host markers shown in column 1. Significant p-values are highlighted.

| Host marker | ESAT6/CFP10 | PHA | PPD | Rv0081 | Rv1733c | Rv2029c | TB18.2 | Un-stimulated |
|---|---|---|---|---|---|---|---|---|
| IFN-γ | 0.0097 | 0.3737 | 0.4280 | 0.5671 | 0.8305 | 0.7658 | 0.0187 | 0.2656 |
| IL-10 | 0.8731 | 0.0151 | 0.0450 | 0.1263 | 0.3180 | 0.7047 | 0.2893 | 0.3092 |
| IL-1β | 0.1807 | 0.6815 | 0.7468 | 0.3721 | 0.8704 | 0.9646 | 0.8195 | 0.9767 |
| IL-6 | 0.8956 | 0.3475 | 0.8315 | 0.0005 | 0.0212 | 0.4221 | 0.6218 | 0.4972 |
| EGF | 0.7452 | 0.7354 | 0.8430 | 0.6037 | 0.8509 | 0.4426 | 0.5774 | 0.1630 |
| eotaxin | 0.7066 | 0.8962 | 0.2921 | 0.2132 | 0.9964 | 0.0313 | 0.0373 | 0.2037 |
| G-CSF | 0.3759 | 0.8066 | 0.8119 | 0.0893 | 0.7553 | 0.3366 | 0.7251 | 0.6283 |
| GM-CSF | 0.0518 | 0.0172 | 0.2705 | 0.9362 | 0.2905 | 0.2641 | 0.0005 | 0.7904 |
| IFN-α2 | 0.1576 | 0.5660 | 0.4347 | 0.7013 | 0.3476 | 0.3086 | 0.1548 | 0.8811 |
| IL-12p40. | 0.0056 | 0.4884 | 0.2318 | 0.9302 | 0.4897 | 0.5780 | 0.9862 | 0.5042 |
| IL-12p70. | 0.0079 | 0.1006 | 0.5845 | 0.9687 | 0.9794 | 0.6879 | 0.0120 | 0.6064 |
| IL-13 | 0.0172 | 0.0165 | 0.0144 | 0.8108 | 0.7027 | 0.0319 | 0.0099 | 0.5923 |
| IL-15 | 0.6350 | 0.4448 | 0.9139 | 0.1228 | 0.1947 | 0.9377 | 0.0005 | 0.6021 |
| IL-17A | 0.6195 | 0.0114 | 0.7177 | 0.8485 | 0.9578 | 0.9845 | 0.1235 | 0.8498 |
| IL-1Ra | 0.5604 | 0.7692 | 0.9351 | 0.0258 | 0.7274 | 0.9115 | 0.0273 | 0.4789 |
| IL-1α | 0.0041 | 0.9614 | 0.9405 | 0.7895 | 0.2374 | 0.0285 | 0.3768 | 0.0079 |
| IL-2 | 0.2882 | 0.4257 | 0.5091 | 0.8197 | 0.2305 | 0.8538 | 0.2554 | 0.9903 |
| IL-3 | 0.6002 | 0.0219 | 0.2415 | 0.3930 | 0.9220 | 0.8909 | 0.3011 | 0.4962 |
| IL-4 |  | 0.0082 | 0.3904 |  |  |  |  |  |
| IL-5 | 0.0798 | 0.0130 | 0.0578 | 0.9174 | 0.7459 | 0.1605 | 0.0079 | 0.8910 |
| IL-7 | 0.8923 | 0.5930 | 0.8799 | 0.6522 | 0.8098 | 0.7776 | 0.7542 | 0.8371 |
| IL-8 | 0.4236 | 0.8799 | 0.8796 | 0.1642 | 0.6566 | 0.5367 | 0.8245 | 0.8184 |
| IP-10 | 0.7827 | 0.6568 | 0.8559 | 0.6139 | 0.5590 | 0.6631 | 0.0848 | 0.5370 |
| MCP-1 | 0.9719 | 0.7444 | 0.6990 | 0.0005 | 0.4515 | 0.2180 | 0.3990 | 0.9422 |
| MIP-1α | 0.0392 | 0.0347 | 0.1825 | 0.0178 | 0.2189 | 0.7264 | 0.9473 | 0.3740 |
| MIP-1β | 0.4620 | 0.1054 | 0.5481 | 0.0005 | 0.0741 | 0.5249 | 0.0921 | 0.3165 |
| TNF-α | 0.1682 | 0.3151 | 0.3395 | 0.0005 | 0.0481 | 0.8038 | 0.4464 | 0.6904 |
| TNF-β | 0.1035 | 0.0135 | 0.3995 | 0.8825 | 0.9422 | 0.3576 | 0.5101 | 0.3494 |
| VEGF | 0.0040 | 0.4672 | 0.0054 | 0.7493 | 0.2317 | 0.3345 | 0.5692 | 0.8176 |
| MCP-2 | 0.0469 | 0.6029 | 0.1703 | 0.2091 | 0.9535 | 0.4189 | 0.5951 | 0.8674 |
| MCP-4 | 0.3155 | 0.8701 | 0.6465 | 0.5949 | 0.5030 | 0.0041 | 0.8083 | 0.0041 |
| ENA-78 | 0.0114 | 0.0146 | 0.0661 | 0.0005 | 0.1424 | 0.0005 | 0.4921 | 0.7909 |
| SDF-1α + β | 0.5095 | 0.4911 | 0.5448 | 0.8361 | 0.5764 | 0.9561 | 0.3441 | 0.5873 |
| BCA-1 | 0.2007 | 0.0007 | 0.7650 | 0.3192 | 0.3915 | 0.7130 | 0.0379 | 0.0085 |
| I-309 | 0.8186 | 0.7833 | 0.6079 | 0.7626 | 0.8499 | 0.3575 | 0.0638 | 0.2859 |
| IL-16 | 0.4324 | 0.4954 | 0.8109 | 0.6201 | 0.3845 | 0.2623 | 0.9970 | 0.3510 |
| MIP-1σ | 0.5953 | 0.6103 | 0.2636 | 0.5780 | 0.7295 | 0.9398 | 0.6666 | 0.8919 |
| TARC | 0.4672 | 0.0189 | 0.0120 | 0.6479 | 0.9361 | 0.8288 | 0.1107 | 0.7501 |
| X6-Ckine | 0.0142 | 0.1716 | 0.4656 | 0.0005 | 0.0175 | 0.0005 | 0.6352 | 0.7589 |
| eotaxin-2 | 0.0312 | 0.2304 | 0.6678 | 0.8179 | 0.5189 | 0.0689 | 0.0086 | 0.1151 |
| eotaxin-3 | 0.5923 | NA | 0.5628 | NA | NA | 0.5923 | NA | NA |
| CTACK | 0.8955 | 0.0590 | 0.0701 | 0.7492 | 0.9330 | 0.0722 | 0.6733 | 0.8576 |
| IL-23 | 0.1505 | 0.3529 | 0.2328 | 0.8976 | 0.2462 | 0.5018 | 0.8195 | 0.7222 |
| LIF | 0.0141 | 0.0137 | 0.3046 | NA | NA | NA | NA | NA |
| TPO | 0.8627 | 0.6008 | 0.1501 | 0.6216 | 0.5763 | 0.9596 | 0.8362 | 0.8520 |
| TRAIL | 0.9248 | 0.0007 | 0.1023 | 0.6314 | 0.8594 | 0.6044 | 0.8781 | 0.9901 |
| SCF | 0.0141 | 0.0166 | 0.0166 | 0.0141 | 0.0120 | 0.0141 | 0.0120 | NA |
| TSLP | 0.7448 | 0.9041 | 0.9889 | 0.9907 | 0.7566 | 0.3658 | 0.9846 | 0.9595 |
| IL-20 | 0.5902 | 0.7509 | 0.6448 | 0.8399 | 0.7129 | 0.5923 | 0.2162 | 0.4305 |
| IL-21 | 0.3862 | 0.0722 | 0.9752 | 0.8558 | 0.3930 | 0.5635 | 0.7157 | 0.6873 |
| IL-28A | 0.4658 | 0.7070 | 0.2044 | 0.9703 | 0.6522 | 0.6795 | 0.7650 | 0.9973 |
| IL-33 | 0.4028 | 0.1149 | 0.9458 | 0.4280 | 0.4106 | 0.7985 | 0.5581 | 0.8408 |
| APOA-1 | 0.1188 | 0.0107 | 0.2080 | 0.6158 | 0.9815 | 0.5307 | 0.1715 | 0.5388 |
| APOC-3 | 0.8878 | 0.2307 | 0.5888 | 0.4436 | 0.7170 | 0.8759 | 0.2231 | 0.0551 |
| APOE | 0.1237 | 0.0007 | 0.0488 | 0.5224 | 0.5436 | 0.2648 | 0.0187 | 0.5715 |
| HPALBN | 0.5961 | 0.0007 | 0.3487 | 0.9820 | 0.8569 | 0.5318 | 0.0108 | 0.0143 |
| HCFH | 0.1606 | 0.0530 | 0.2899 | 0.5622 | 0.6492 | 0.3748 | 0.3282 | 0.0108 |
| HCC3 | 0.1027 | 0.0871 | 0.0890 | 0.7641 | 0.8043 | 0.2384 | 0.2509 | 0.2438 |
| HA2MG | 0.4548 | 0.0889 | 0.1723 | 0.6852 | 0.9011 | 0.6159 | 0.7387 | 0.4781 |
| CRP | 0.7876 | 0.2421 | 0.2006 | 0.8040 | 0.6926 | 0.9093 | 0.0301 | 0.0005 |

TABLE 8-continued

Abilities of novel antigen-specific host markers to discriminate between individuals with pulmonary TB disease and no TB. The values under the different antigens represent the p-values for the host markers shown in column 1. Significant p-values are highlighted.

| Host marker | ESAT6/ CFP10 | PHA | PPD | Rv0081 | Rv1733c | Rv2029c | TB18.2 | Un-stimulated |
|---|---|---|---|---|---|---|---|---|
| SAA | 0.5274 | 0.2981 | 0.3942 | 0.7325 | 0.8710 | 0.7331 | 0.0234 | 0.0046 |
| SAP | 0.1899 | 0.1840 | 0.1335 | 0.6165 | 0.5491 | 0.5370 | 0.2137 | 0.0005 |
| TIMP-1 | 0.0659 | 0.1893 | 0.3745 | 0.1760 | 0.2297 | 0.1280 | 0.0498 | 0.0005 |
| TIMP-2 | 0.3911 | 0.1764 | 0.3453 | 0.5771 | 0.2557 | 0.0617 | 0.8588 | 0.4855 |
| TIMP-3 | 0.8393 | 0.0778 | 0.7931 | 0.7474 | 0.2383 | 0.4364 | 0.9848 | 0.8109 |
| TIMP-4 | 0.9339 | 0.2131 | 0.5558 | 0.5714 | 0.8719 | 0.5320 | 0.1731 | 0.3544 |
| MMP-2 | 0.8633 | 0.1190 | 0.5307 | 0.4858 | 0.1621 | 0.1067 | 0.5867 | 0.2188 |
| MMP-9 | 0.9238 | 0.8270 | 0.9873 | 0.3600 | 0.9883 | 0.8630 | 0.7198 | 0.3016 |
| IL-17F | 0.4536 | 0.0347 | 0.0732 | 0.9590 | 0.4167 | 0.7446 | 0.7224 | 0.0626 |
| IL-22 | 0.0938 | 0.0692 | 0.0813 | 0.5780 | 0.0109 | 0.8265 | 0.7803 | 0.8334 |
| IL-17E/IL-25 | 0.4824 | 0.6188 | 0.4282 | 0.1498 | 0.9745 | 0.1154 | 0.1309 | 0.9444 |
| IL-27 | 0.8865 | 0.9341 | 0.9097 | 0.6318 | 0.7532 | 0.4081 | 0.6106 | 0.4501 |
| IL-31 | 0.5736 | 0.7785 | 0.6519 | 0.8940 | 0.3906 | 0.3844 | 0.9154 | 0.2240 |

TABLE 9

Accuracy of novel host markers identified in overnight (in-house) whole blood culture supernatants in the diagnosis of TB disease. The values shown for each antigen-specific host marker are the AUC, expressed as a fraction. Antigen-specific markers that diagnosed TB disease with an accuracy of 100% (AUC = 1) are highlighted.

| | ESAT6/ CFP1 0 | PHA | PPD | Rv0081 | Rv1733c | Rv2029c | TB18.2 | Un-stimulated |
|---|---|---|---|---|---|---|---|---|
| IFN-γ | 0.97 | 0.86 | 0.94 | 0.92 | 0.89 | 0.91 | 0.95 | 0.94 |
| IL-10 | 0.89 | 0.98 | 0.96 | 0.97 | 0.92 | 0.89 | 0.88 | 0.89 |
| IL-1β | 0.89 | 0.86 | 0.94 | 0.89 | 0.88 | 0.89 | 0.82 | 0.88 |
| IL-6 | 0.91 | 0.86 | 0.86 | _1_ | 0.97 | 0.94 | 0.88 | 0.91 |
| EGF | 0.89 | 0.88 | 0.84 | 0.91 | 0.88 | 0.89 | 0.91 | 0.94 |
| eotaxin | 0.92 | 0.86 | 0.9 | 0.92 | 0.86 | 0.95 | 0.91 | 0.94 |
| G-CSF | 0.89 | 0.88 | 0.82 | 0.95 | 0.89 | 0.9 | 0.86 | 0.9 |
| GM-CSF | 0.94 | 0.92 | 0.92 | 0.89 | 0.92 | 0.94 | _1_ | 0.89 |
| IFN-α2 | 0.91 | 0.88 | 0.88 | 0.91 | 0.94 | 0.93 | 0.93 | 0.82 |
| IL-12p40 | 0.97 | 0.91 | 0.94 | 0.84 | 0.88 | 0.9 | 0.88 | 0.84 |
| IL-12p70 | 0.97 | 0.9 | 0.9 | 0.88 | 0.89 | 0.89 | 0.95 | 0.88 |
| IL-13 | 0.95 | 0.92 | 0.96 | 0.84 | 0.91 | 0.94 | 0.96 | 0.83 |
| IL-15 | 0.89 | 0.86 | 0.9 | 0.94 | 0.89 | 0.94 | _1_ | 0.89 |
| IL-17A | 0.94 | 0.98 | 0.9 | 0.88 | 0.84 | 0.84 | 0.95 | 0.91 |
| IL-1 Ra | 0.89 | 0.84 | 0.86 | 0.94 | 0.89 | 0.91 | 0.97 | 0.94 |
| IL-1α | 0.98 | 0.9 | 0.94 | 0.85 | 0.94 | 0.95 | 0.92 | 0.97 |
| IL-2 | 0.94 | 0.88 | 0.9 | 0.86 | 0.94 | 0.88 | 0.95 | 0.88 |
| IL-3 | 0.88 | 0.92 | 0.9 | 0.97 | 0.91 | 0.88 | 0.97 | 0.88 |
| IL-4 | 0.82 | 0.97 | 0.82 | 0.82 | 0.82 | 0.82 | 0.82 | 0.82 |
| IL-5 | 0.92 | 0.96 | 0.92 | 0.92 | 0.92 | 0.92 | 0.97 | 0.88 |
| IL-7 | 0.88 | 0.9 | 0.85 | 0.88 | 0.88 | 0.89 | 0.88 | 0.83 |
| IL-8 | 0.88 | 0.88 | 0.86 | 0.95 | 0.91 | 0.88 | 0.86 | 0.88 |
| IP-10 | 0.92 | 0.9 | 0.88 | 0.86 | 0.88 | 0.88 | 0.95 | 0.92 |
| MCP-1 | 0.89 | 0.86 | 0.88 | _1_ | 0.86 | 0.89 | 0.95 | 0.88 |
| MIP-1α | 0.94 | 0.9 | 0.92 | 0.97 | 0.91 | 0.86 | 0.89 | 0.92 |
| MIP-1β | 0.89 | 0.86 | 0.88 | _1_ | 0.95 | 0.89 | 0.95 | 0.95 |
| TNF-α | 0.94 | 0.86 | 0.96 | _1_ | 0.95 | 0.89 | 0.92 | 0.86 |
| TNF-β | 0.95 | 0.95 | 0.91 | 0.89 | 0.87 | 0.91 | 0.88 | 0.84 |
| VEGF | 0.98 | 0.9 | 0.98 | 0.85 | 0.91 | 0.95 | 0.86 | 0.93 |
| MCP-2 | 0.95 | 0.84 | 0.92 | 0.94 | 0.88 | 0.91 | 0.94 | 0.91 |
| MCP-4 | 0.94 | 0.88 | 0.88 | 0.91 | 0.94 | 0.98 | 0.9 | 0.98 |
| ENA-78 | 0.95 | 0.94 | 0.9 | _1_ | 0.95 | _1_ | 0.94 | 0.88 |
| SDF-1α + β | 0.91 | 0.88 | 0.94 | 0.86 | 0.88 | 0.89 | 0.91 | 0.89 |
| BCA -1 | 0.92 | _1_ | 0.8 | 0.89 | 0.89 | 0.88 | 0.92 | 0.97 |
| I-309 | 0.9 | 0.9 | 0.85 | 0.88 | 0.89 | 0.91 | 0.93 | 0.91 |
| IL-16 | 0.92 | 0.92 | 0.9 | 0.92 | 0.92 | 0.94 | 0.88 | 0.97 |
| MIP-1δ | 0.89 | 0.88 | 0.9 | 0.92 | 0.88 | 0.88 | 0.89 | 0.88 |
| TARC | 0.91 | 0.94 | 0.98 | 0.89 | 0.86 | 0.88 | 0.91 | 0.92 |
| X6-Ckine | 0.97 | 0.88 | 0.88 | _1_ | 0. 8 | _1_ | 0.9 | 0.88 |
| eotaxin-2 | 0.92 | 0.92 | 0.92 | 0.89 | 0.91 | 0.89 | 0.97 | 0.94 |
| eotaxin-3 | 0.88 | 0.8 | 0.87 | 0.82 | 0.82 | 0.88 | 0.82 | 0.82 |

TABLE 9-continued

Accuracy of novel host markers identified in overnight (in-house) whole blood culture supernatants in the diagnosis of TB disease. The values shown for each antigen-specific host marker are the AUC, expressed as a fraction. Antigen-specific markers that diagnosed TB disease with an accuracy of 100% (AUC = 1) are highlighted.

|   | ESAT6/CFP10 | PHA | PPD | Rv0081 | Rv1733c | Rv2029c | TB18.2 | Un-stimulated |
|---|---|---|---|---|---|---|---|---|
| CTACK | 0.89 | 0.94 | 0.92 | 0.88 | 0.88 | 0.95 | 0.89 | 0.89 |
| IL-23 | 0.92 | 0.94 | 0.94 | 0.86 | 0.92 | 0.89 | 0.86 | 0.92 |
| LIF | 0.95 | 0.95 | 0.95 | 0.82 | 0.82 | 0.82 | 0.82 | 0.82 |
| TPO | 0.84 | 0.92 | 0.92 | 0.88 | 0.88 | 0.88 | 0.88 | 0.89 |
| TRAIL | 0.84 | _1_ | 0.94 | 0.91 | 0.91 | 0.91 | 0.88 | 0.89 |
| SCF | 0.95 | 0.94 | 0.94 | 0.95 | 0.95 | 0.95 | 0.95 | 0.82 |
| TSLP | 0.88 | 0.9 | 0.84 | 0.91 | 0.88 | 0.92 | 0.88 | 0.86 |
| IL-20 | 0.84 | 0.82 | 0.83 | 0.83 | 0.83 | 0.83 | 0.85 | 0.84 |
| IL-21 | 0.88 | 0.86 | 0.84 | 0.92 | 0.95 | 0.89 | 0.84 | 0.9 |
| IL-28A | 0.9 | 0.86 | 0.9 | 0.88 | 0.89 | 0.9 | 0.91 | 0.86 |
| IL-33 | 0.9 | 0.92 | 0.81 | 0.91 | 0.89 | 0.88 | 0.89 | 0.84 |
| APOA-1 | 0.95 | 0.98 | 0.94 | 0.91 | 0.86 | 0.94 | 0.95 | 0.89 |
| APOC-3 | 0.88 | 0.9 | 0.9 | 0.89 | 0.88 | 0.88 | 0.89 | 0.92 |
| APOE | 0.91 | _1_ | 0.92 | 0.88 | 0.89 | 0.94 | 0.95 | 0.89 |
| HPALBN | 0.88 | _1_ | 0.9 | 0.88 | 0.88 | 0.91 | 0.98 | 0.98 |
| HCFH | 0.97 | 0.96 | 0.92 | 0.92 | 0.91 | 0.94 | 0.86 | 0.97 |
| HCC3 | 0.97 | 0.94 | 0.94 | 0.88 | 0.89 | 0.91 | 0.94 | 0.89 |
| HA2MG | 0.89 | 0.96 | 0.92 | 0.89 | 0.88 | 0.91 | 0.86 | 0.88 |
| CRP | 0.91 | 0.94 | 0.92 | 0.89 | 0.94 | 0.84 | 0.88 | _1_ |
| SAA | 0.94 | 0.94 | 0.94 | 0.88 | 0.94 | 0.91 | 0.89 | 0.98 |
| SAP | 0.95 | 0.94 | 0.94 | 0.89 | 0.92 | 0.94 | 0.89 | _1_ |
| TIMP-1 | 0.95 | 0.92 | 0.92 | 0.94 | 0.92 | 0.94 | 0.91 | _1_ |
| TIMP-2 | 0.91 | 0.94 | 0.88 | 0.89 | 0.89 | 0.92 | 0.91 | 0.91 |
| TIMP-3 | 0.91 | 0.92 | 0.94 | 0.88 | 0.94 | 0.92 | 0.88 | 0.89 |
| TIMP-4 | 0.84 | 0.94 | 0.92 | 0.95 | 0.83 | 0.95 | 0.94 | 0.91 |
| MMP-2 | 0.88 | 0.92 | 0.89 | 0.92 | 0.95 | 0.94 | 0.88 | 0.94 |
| MMP-9 | 0.88 | 0.86 | 0.88 | 0.91 | 0.9 | 0.9 | 0.86 | 0.91 |
| IL-17F | 0.89 | 0.92 | 0.89 | 0.91 | 0.94 | 0.86 | 0.93 | 0.97 |
| IL-22 | 0.88 | 0.86 | 0.91 | 0.9 | 0.96 | 0.84 | 0.94 | 0.89 |
| IL-17E/IL-25 | 0.88 | 0.86 | 0.86 | 0.91 | 0.87 | 0.88 | 0.89 | 0.91 |
| IL-27 | 0.88 | 0.86 | 0.86 | 0.89 | 0.85 | 0.86 | 0.89 | 0.91 |
| IL-31 | 0.89 | 0.86 | 0.86 | 0.88 | 0.93 | 0.86 | 0.91 | 0.92 |
| Total with AUC of 1 | 0 | 4 | 0 | 6 | 0 | 2 | 2 | 3 |

Figure 5:
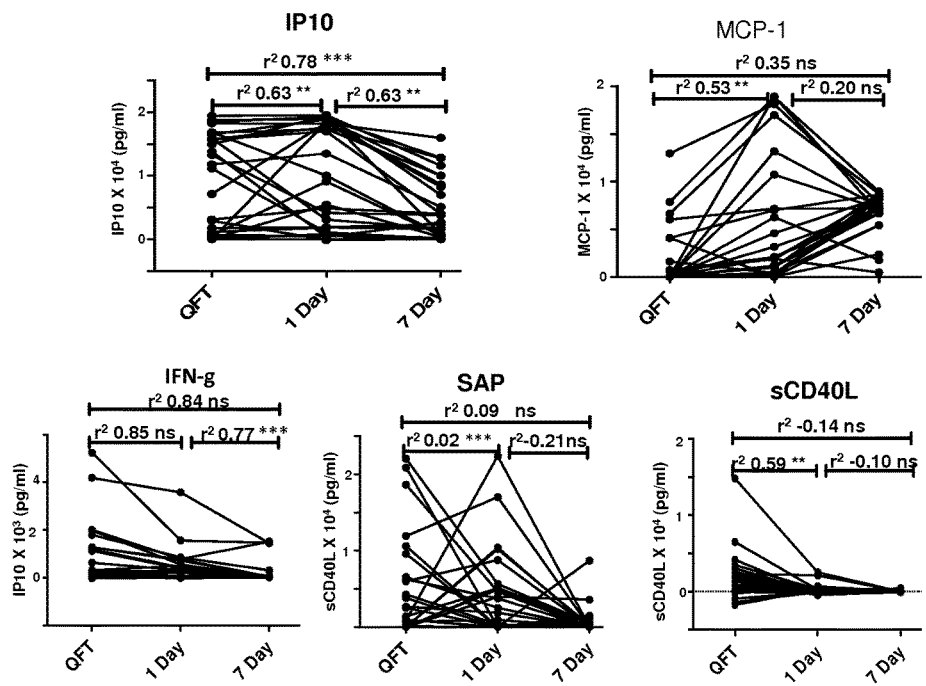
FIG. 5: Correlation between analytes detected by the three whole blood assay types after stimulation with ESAT-6/CFP-10. Representative plots for five ESAT-6/CFP-10-induced host markers are shown. ns=non-significant, *=P value<0.05, =P value≤0.001, *=P value<0.0001.
Figure 6:
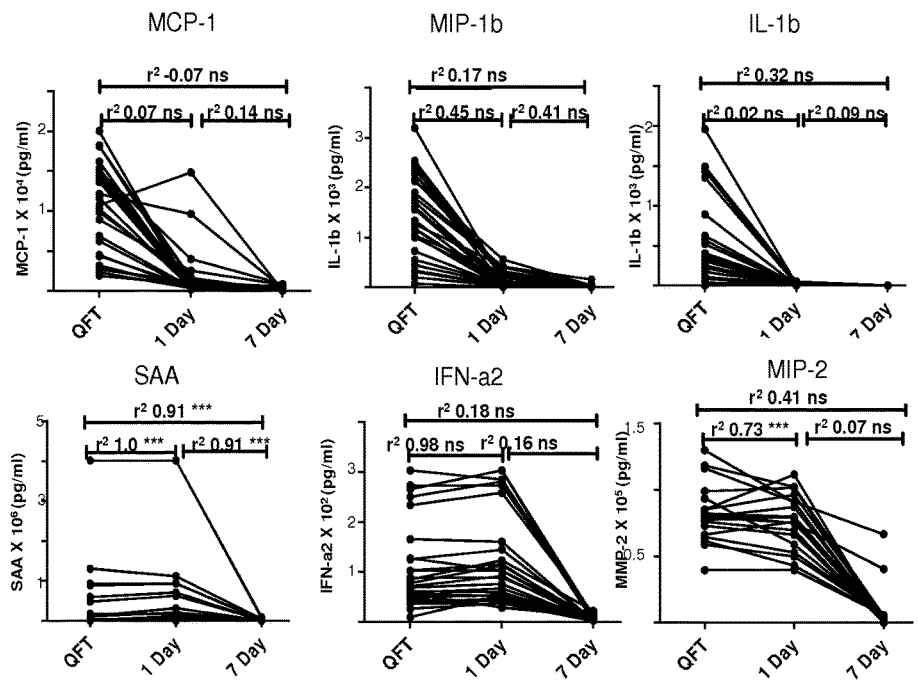
FIG. 6: Correlation between analytes detected in unstimulated supernatants in the three whole blood assay types. Representative plots for six host markers are shown. ns=non-significant, *=P value<0.05, =P value≤0.001, *=P value<0.0001.

In general, unstimulated and antigen-stimulated analyte levels were lower in the 7-day WBA in comparison to the QFT-IT and the applicant's in-house overnight WBA (FIGS. 5 and 6). Of the 26 analytes evaluated, 12 (fractalkine, IFN-α2, MCP-1, MIP-1β, VEGF, IL-1β, IL-10, MMP-2, MMP-9, CRP, SAA and SAP) showed significant differences between TB disease and no-disease when evaluated in unstimulated supernatants. The levels of VEGF, MMP-2, CRP, SAA, SAP and fractalkine obtained in the unstimulated QFT-IT supernatants were generally similar to the levels obtained in the in-house WBA. With exception of fractalkine, all unstimulated analyte levels were significantly lower (2-200 fold) in the 7-day WBA supernatants in comparison to either the QFT-IT or the in-house overnight WBA. Similarly, there were generally no significant differences in the levels of markers upon stimulation with ESAT-6/CFP-10 between the QFT-IT and the in-house overnight WBA, but generally lower levels were obtained in the 7-day stimulated supernatants (Table 10). ESAT-6/CFP10-specific IP-10 and unstimulated SAA were the only common discriminatory markers between TB disease and no TB in all three assay types (Tables 2, 4 and 6). Interestingly, these 2 analytes showed a significant positive correlation between all the three assays types ($r^2=1$, $p<0.0001$ in some cases). Again, the highest correlations were observed between the QFT-IT and the in-house overnight WBA responses (Table 10, FIGS. 5 and 6).

Discussion

The diagnostic potential of host markers detectable in supernatants after overnight or 7-day whole blood stimulation with M.tb infection-phase-dependent antigens was evaluated in this study. It was shown that the novel M.tb infection-phase-dependent antigens evaluated in this study elicit a variety of host responses after short-term incubation with whole blood. This confirms the suitability of these antigens and associated host markers for use as diagnostic candidates for TB disease. The potentially useful diagnostic host markers induced by these antigens include acute phase proteins, cytokines, chemokines, growth factors and matrix metallo-proteinases. The most promising candidate markers are unstimulated SAA, CRP, SAP, IP-10, MMP-9, EGF, MMP-2, MMP-9 and TIMP-1; ESAT-6/CFP10-induced IP-10 and sCD40L; Rv2032-induced MMP-2; Rv0081-specific IL-6, MCP-1, MIP-1β, TNF-α, ENA-78, X6-Ckine; Rv2029c-specific ENA-78 and X6-Ckine; TB18.2-specific GM-CSF and IL-15.

TABLE 10

Correlation between ESAT-6/CFP-10-specific and unstimulated analyte
levels detected in the three whole blood assay (WBA) types.

|  | QFT vs 1 day | | QFT vs 7 day | | 1 day vs 7 day | | Fold difference | |
|---|---|---|---|---|---|---|---|---|
|  | | | | | | | QFT vs | QFT vs |
|  | $r^2$ | P value | $r^2$ | P value | $r^2$ | P value | overnight | 7-day WBA |
| ESAT6/CFP10 IP10 | 0.63 | 0.0004 | 0.60 | 0.001 | 0.78 | <0.0001 | 1.3 | 4.4 |
|  |  | 0.5984049 |  |  |  |  |  |  |
| ESAT6/CFP10 MCP-1 | 0.53 | 0.004 | 0.35 | 0.076 | 0.20 | 0.31 | 0.0005 | 0.0001 |
| ESAT6/CFP10 IFN-γ | 0.85 | 1.44 | 0.84 | 3.96 | 0.77 | <0.0001 | 2.5 | 179 |
| ESAT6/CFP10 EGF | −0.16 | 0.41 | −0.20 | 0.31 | 0.29 | 0.15 | 1 | 1 |
| ESAT6/CFP10 MMP-9 | 0.62 | 0.002 | 0.19 | 0.40 | 0.19 | 0.40 | 1.4 | 1.3 |
| ESAT6/CFP10 sCD40L | 0.05 | 0.78 | −0.15 | 0.44 | −0.01 | 0.97 | 8.1 | 39.1 |
| ESAT6/CFP10 SAP | 0.74 | <0.0001 | 0.06 | 0.75 | 0.15 | 0.43 | 0.75 | 15.7 |
| Unstimulated Fractalkine | 0.40 | 0.031 | 0.42 | 0.021 | 016 | 0.41 | 0.5 | 1.1 |
| Unstimulated IFN-α2 | 0.98 | <0.0001 | 0.18 | 0.35 | 0.16 | 0.40 | 2 | 5.7 |
| Unstimulated MCP-1 | 0.07 | 0.73 | −0.07 | 0.72 | 0.14 | 0.47 | 15 | 200 |
| Unstimulated MIP-1β | 0.45 | 0.015 | 0.17 | 0.39 | 0.41 | 0.03 | 109 | 746 |
| Unstimulated VEGF | 0.32 | 0.096 | 0.08 | 0.68 | 0.26 | 0.17 | 1.3 | 4.7 |
| Unstimulated IL-1β | 0.65 | 0.0001 | 0.12 | 0.55 | 0.40 | 0.03 | 115 | 115 |
| Unstimulated IL-10 | 0.63 | 0.0003 | −0.18 | 0.36 | −0.15 | 0.43 | 2 | 5.7 |
| Unstimulated MMP-2 | 0.73 | 0.0001 | 0.41 | 0.06 | 0.07 | 0.76 | 1 | 23 |
| Unstimulated MMP-9 | 0.62 | 0.002 | 0.19 | 0.40 | 0.19 | 0.41 | 2.4 | 13.5 |
| Unstimulated CRP | 0.95 | <0.0001 | 0.38 | 0.044 | 0.40 | 0.033 | 1.1 | 39.8 |
| Unstimulated SAA | 1.0 | <0.0001 | 0.91 | <0.0001 | 0.90 | <0.0001 | 0.7 | 39 |
| Unstimulated SAP | 0.74 | <0.0001 | 0.06 | 0.75 | 0.15 | 0.43 | 1.2 | 36.3 |

Only analytes that discriminated between TB and no-TB with AUC >0.70 in at least one of the WBA types are shown.
All analytes with R square value above 0.5 and p value <0.01 are highlighted bold.
The mean value on these markers were computed and compared between assays.

There was generally a good correlation between the markers detected using the in-house overnight WBA and those detected using the QFT-IT assay and this is not surprising. The magnitude of responses obtained with the two overnight assays was consistently higher than the responses obtained in the 7-day WBAs. This could be explained by the amount of sample that was used in the different assay types. The two overnight assays (the in-house overnight WBA and the QFT-IT assay) employed 1 ml of undiluted whole blood while blood samples were diluted five times before being evaluated in the 7-day WBA, as is standard practice[15]. The excellent correlation between the in-house assay and the QFT-IT test, a well-standardised assay that is considered in some settings as the "gold standard" for LTBI, means that the promising antigens and associated host markers detected using the in-house WBA have excellent potential to be useful in the diagnosis of TB disease. However, direct comparison of performance of the three assay types could only be possible for the markers detected in unstimulated samples and those detected in ESAT-6/CFP-10 stimulated supernatants. The QFT-IT assay employs a third antigen (TB7.7) in addition to ESAT-6/CFP-10, and therefore the marginally higher responses that were obtained in QFT-IT supernatants could be due to markers produced in response to this third antigen, as ESAT-6 and CFP-10 were the only two antigens in our RD-1 fusion protein.

IFN-γ release assays (IGRAs) are well established and remain the assays of choice for the diagnosis of LTBI in many settings. However, these assays do not discriminate between LTBI and active disease and are therefore not recommended in high burden settings. This is mainly because of the large proportion of LTBI cases in high-burden settings, coupled with limited resources[26]. The current study was performed in a setting with a high burden of TB. The results indicate that diagnostic tests that are based on these antigens and host markers might be highly suitable in high-burden settings. It is envisaged that diagnostic tests based on these novel antigens and novel host markers will mostly be beneficial to TB control programs if such antigens and markers are incorporated into rapid, point-of-care test platforms such as the lateral flow technology. Such testing platforms are currently being investigated by the applicant.

CONCLUSION

In conclusion, the results of the current study show that the markers reported herein show promise in the diagnosis of TB disease. Furthermore, additional markers such as CRP, SAA, SAP, sCD40L, MMP-2, MMP-9, IL-6, MCP-1, MIP-1β, TNF-α, ENA-78, X6-Ckine, GM-CSF and IL-15, amongst others, as shown in the Tables 6 to 9, might also be useful in the diagnosis of TB disease if measured in unstimulated supernatants or whole blood culture supernatants after stimulation with infection-phase-dependent antigens, including Rv0081, ESAT-6/CFP-10, Rv2029c, Rv1733c, TB18.2, Rv0081, Rv2032, Rv1737c, Rv2389c, Rv0867c, in short-term culture assays. These data could form the basis for the development of a novel immunodiagnostic test for TB disease.

REFERENCES

1. WHO 2009. Global Tuberculosis Control: Epidemiology, Strategy, Financing. Ref type at <http://whqlibdoc.who.int/publications/2009/9789241563802_eng.pdf>
2. Chegou, N. N. et al. Tuberculosis assays: past, present and future. *Expert Rev Anti Infect Ther* 9, 457-469 (2011).
3. Verweij, K. E. et al. Application of modern microbiological diagnostic methods for tuberculosis in Macha, Zambia. *Int. J. Tuberc. Lung Dis.* 14, 1127-1131 (2010).
4. Dowdy, D. W. et al. Impact and cost-effectiveness of culture for diagnosis of tuberculosis in HIV-infected Brazilian adults. *PLoS ONE* 3, e4057 (2008).

5. Steingart, K. R. et al. in *Cochrane Database of Systematic Reviews* (John Wiley & Sons, Ltd, 1996). at <http://onlinelibrary.wiley.com/doi/10.1002/14651858.CD009593.pub2/abstract>
6. Kirwan, D. E., Cárdenas, M. K. & Gilman, R. H. Rapid Implementation of New TB Diagnostic Tests: Is It Too Soon for a Global Roll-Out of Xpert MTB/RIF? *Am. J. Trop. Med. Hyg.* 87, 197-201 (2012).
7. Trébucq, A. et al. Xpert® MTB/RIF for national tuberculosis programmes in low-income countries: when, where and how? *Int. J. Tuberc. Lung Dis.* 15, 1567-1572 (2011).
8. Chegou, N. N., Walzl, G., Bolliger, C. T., Diacon, A. H. & van den Heuvel, M. M. Evaluation of adapted whole-blood interferon-gamma release assays for the diagnosis of pleural tuberculosis. *Respiration* 76, 131-138 (2008).
9. Chegou, N. N. et al. Utility of Host Markers Detected in Quantiferon Supernatants for the Diagnosis of Tuberculosis in Children in a High-Burden Setting. *PLoS ONE* 8, e64226 (2013).
10. Steingart, K. R., Ramsay, A., Dowdy, D. W. & Pai, M. Serological tests for the diagnosis of active tuberculosis: relevance for India. *Indian J. Med. Res.* 135, 695-702 (2012).
11. *WHO report* 2012.
12. Sester, M. et al. Interferon-γ release assays for the diagnosis of active tuberculosis: a systematic review and meta-analysis. *Eur. Respir. J.* 37, 100-111 (2011).
13. World Health Organization. Use of tuberculosis interferon-gamma release assays (IGRAs) in low- and middle-income countries: policy statement. (2011).
14. WHO|Global tuberculosis report 2012. *WHO* at <http://www.who.int/tb/publications/global_report/en/>
15. Pai, M. & Menzies, D. The new IGRA and the old TST: making good use of disagreement. *Am. J. Respir. Crit. Care Med.* 175, 529-531 (2007).
16. Chegou, N. N. et al. Potential of novel *Mycobacterium tuberculosis* infection phase-dependent antigens in the diagnosis of TB disease in a high burden setting. *BMC Infect. Dis.* 12, 10 (2012).
17. Schuck, S. D. et al. dentification of T-Cell Antigens Specific for Latent *Mycobacterium Tuberculosis* Infection. *PLoS ONE* 4, e5590 (2009).
18. Commandeur, S. et al. Identification of Human T-Cell Responses to *Mycobacterium tuberculosis* Resuscitation-Promoting Factors in Long-Term Latently Infected Individuals ∇. *Clin Vaccine Immunol* 18, 676-683 (2011).
19. Kashyap, R. S. et al. Diagnosis of tuberculosis infection based on synthetic peptides from *Mycobacterium tuberculosis* antigen 85 complex. *Clinical Neurology and Neurosurgery* (2012). doi:10.1016/j.clineuro.2012.07.031
20. Govender, L. et al. Higher human CD4 T cell response to novel *Mycobacterium tuberculosis* latency associated antigens Rv2660 and Rv2659 in latent infection compared with tuberculosis disease. *Vaccine* 29, 51-57 (2010).
21. Sk, R., Sw, S., Sp, M., Jp, H. & Mt, G. *Mycobacterium Tuberculosis* Heat Shock Protein 16 as a Potential Marker for Latent TB: A Preliminary Findings. *Journal of Clinical & Cellular Immunology* 02, (2011).
22. Chiacchio, T. et al. Higher Frequency of T-Cell Response to *M. tuberculosis* Latency Antigen Rv2628 at the Site of Active Tuberculosis Disease than in Peripheral Blood. *PLoS ONE* 6, e27539 (2011).
23. Dosanjh, D. P. S. et al. Novel *M tuberculosis* Antigen-Specific T-Cells Are Early Markers of Infection and Disease Progression. *PLoS ONE* 6, e28754 (2011).
24. Chegou, N. N., Black, G. F., Kidd, M., van Heden, P. D. & Walzl, G. Host markers in QuantiFERON supernatants differentiate active TB from latent TB infection: preliminary report. *BMC Pulm Med* 9, 21 (2009).
25. Chegou, N. N. et al. Potential of host markers produced by infection phase-dependent antigen-stimulated cells for the diagnosis of tuberculosis in a highly endemic area. *PLoS ONE* 7, e38501 (2012).
26. Chegou, N. N., Black, G. F., Kidd, M., van Heden, P. D. & Walzl, G. Host markers in QuantiFERON supernatants differentiate active TB from latent TB infection: preliminary report. *BMC Pulm Med* 9, 21 (2009).
27. Black, G. F. et al. Immunogenicity of novel DosR regulon-encoded candidate antigens of *Mycobacterium tuberculosis* in three high-burden populations in Africa. *Clin. Vaccine Immunol.* 16, 1203-1212 (2009).

Funding

This work was supported by the EDCTP through the African European-Tuberculosis Consortium (AE-TBC) (www.ae-tbc.eu), Principal Investigator Prof. Gerhard Walzl. The funders had no role in study design, data collection and analysis, decision to patent and publish, or preparation of the manuscript.

The invention claimed is:

1. A method of diagnosing tuberculosis (TB) disease in a subject, the method comprising the steps of:
   separately contacting identical samples from the subject with each of Rv0081 antigen, ESAT-6/CFP-10 antigen, and TB18.2 antigen, wherein the samples comprise immune cells from the subject; and
   testing the samples for the presence or the absence of at least three antigen-specific host markers induced by the Rv0081 antigen, the ESAT-6/CFP-10 antigen, and the TB18.2 antigen when the subject has active TB disease, wherein the at least three host markers are selected from the group consisting of Rv0081 stimulated SAA, ESAT-6/CFP-10 stimulated IFN-γ, TB18.2 stimulated CRP, Rv0081 stimulated IL-10, Rv0081 stimulated IP-10, Rv0081 stimulated SCF, Rv0081 stimulated MCP-1, Rv0081 stimulated CRP, Rv0081 stimulated IL-13, TB18.2 stimulated IP-10, TB18.2 stimulated HA2MG (alpha-2-macroglobulin), TB18.2 stimulated MCP-1, TB18.2 stimulated VEGF, TB18.2 stimulated X6-Ckine, TB18.2 stimulated MIP-1α, TB18.2 stimulated SAA, ESAT-6/CFP-10 stimulated ENA-78 and ESAT-6/CFP-10 stimulated IP-10; and
   wherein the presence of at least one of the host markers indicates that the subject has TB disease and wherein the method of diagnosis discriminates between latent *Mycobacterium tuberculosis* infection and active TB disease in the subject.

2. The method according to claim 1, wherein the method further comprises the step of detecting the presence or absence of one or more unstimulated host markers in the sample before the sample is contacted with the antigens.

3. A kit for use in a method of diagnosing tuberculosis (TB), the kit comprising:
   *Mycobacterium tuberculosis* (M.tb) infection phase-dependent antigens Rv0081, TB18.2, and ESAT-6/CFP-10; and
   means for detecting the presence of at least three markers selected from the group consisting of SAA, IFN-γ, CRP, IL-10, IP-10, SCF, MCP-1, IL-13, HA2MG (alpha-2-macroglobulin), VEGF, X6-Ckine, MIP-1a, and ENA-78.

4. The kit according to claim 3, which further comprises three separate receptacles into which the samples from the subject can be placed, wherein each of the antigens are located in one of the three separate receptacles.

5. The method according to claim 1, wherein the at least three host markers are:
Rv0081 stimulated SAA,
ESAT-6/CFP-10 stimulated IFN-γ and
TB18.2 stimulated CRP.

6. The method according to claim 2, which comprises detecting the presence or absence of:
Rv0081 stimulated SAA,
ESAT-6/CFP-10 stimulated IFN-γ,
TB18.2 stimulated CRP and
IP-10.

7. The method according to claim 5, which comprises detecting the presence or absence of at least four antigen-specific host markers, the four antigen-specific host markers being:
Rv0081 stimulated SAA,
ESAT-6/CFP-10 stimulated IFN-γ,
TB18.2 stimulated CRP and
ESAT-6/CFP-10 stimulated IP-10.

8. The method according to claim 1, wherein the antigen-specific host markers are detected after the sample has been contacted with the antigens overnight.

9. The method according to claim 1, wherein the antigen-specific host markers are detected after the sample has been contacted with the antigens for 7 days.

10. The kit according to claim 3, wherein the means for detecting the presence of the markers are antibodies.

11. The kit according to claim 3, which comprises means for detecting the following markers:
SAA,
IFN-γ and
CRP.

12. The kit according to claim 11, further comprising means for detecting IP-10.

13. The kit according to claim 3, which comprises means for detecting the presence or absence of at least four markers, the four markers being:
SAA,
IFN-γ,
CRP and
IP-10.

14. A method comprising the steps of:
separately contacting identical samples from a subject with Rv0081 antigen, ESAT-6/CFP-10 antigen, and TB18.2 antigen, wherein the sample comprises immune cells from the subject; and
testing the samples for the presence or the absence in the sample of at least three antigen-specific host markers induced by the Rv0081 antigen, the ESAT-6/CFP-10 antigen, and the TB18.2 antigen;
wherein the at least three host markers are selected from the group consisting of Rv0081 stimulated SAA, ESAT-6/CFP-10 stimulated IFN-γ, TB18.2 stimulated CRP, Rv0081 stimulated IL-10, Rv0081 stimulated IP-10, Rv0081 stimulated SCF, Rv0081 stimulated MCP-1, Rv0081 stimulated CRP, Rv0081 stimulated IL-13, TB18.2 stimulated IP-10, TB18.2 stimulated HA2MG (alpha-2-macroglobulin), TB18.2 stimulated MCP-1, TB18.2 stimulated VEGF, TB18.2 stimulated X6-Ckine, TB18.2 stimulated MIP-1a, TB18.2 stimulated SAA, ESAT-6/CFP-10 stimulated ENA-78 and ESAT-6/CFP-10 stimulated IP-10.

15. The method according to claim 14, wherein the method further comprises the step of detecting the presence or absence of one or more unstimulated host markers in the sample before the sample is contacted with the antigens.

16. The method according to claim 14, wherein the at least three host markers are:
Rv0081 stimulated SAA,
ESAT-6/CFP-10 stimulated IFN-γ and
TB18.2 stimulated CRP.

17. The method according to claim 15, which comprises detecting the presence or absence of:
Rv0081 stimulated SAA,
ESAT-6/CFP-10 stimulated IFN-γ,
TB18.2 stimulated CRP.

18. The method according to claim 16, which comprises detecting the presence or absence of at least four antigen-specific host markers, the four antigen-specific host markers being:
Rv0081 stimulated SAA,
ESAT-6/CFP-10 stimulated IFN-γ,
TB18.2 stimulated CRP and
ESAT-6/CFP-10 stimulated IP-10.

19. The method according to claim 14, wherein the antigen-specific host markers are detected after the sample has been contacted with the antigens overnight or the antigen-specific host markers are detected after the sample has been contacted with the antigens for 7 days.

* * * * *